(12) United States Patent
Li et al.

(10) Patent No.: US 10,568,642 B2
(45) Date of Patent: Feb. 25, 2020

(54) BONE SURGERY GRINDING EXPERIMENTAL DEVICE CAPABLE OF COOLING AND ELECTROSTATIC ATOMIZATION FILM FORMATION

(71) Applicant: QINGDAO TECHNOLOGY UNIVERSITY, Qingdao, Shandong (CN)

(72) Inventors: Changhe Li, Qingdao (CN); Min Yang, Qingdao (CN); Yanbin Zhang, Qingdao (CN); Runze Li, Qingdao (CN); Jun Wang, Qingdao (CN); Yali Hou, Qingdao (CN); Yaogang Wang, Qingdao (CN); Benkai Li, Qingdao (CN); Guotao Liu, Qingdao (CN)

(73) Assignee: QINGDAO TECHNOLOGICAL UNIVERSITY, Qingdao, Shandong (CN)

( * ) Notice: Subject to any disclaimer, the term of this patent is extended or adjusted under 35 U.S.C. 154(b) by 242 days.

(21) Appl. No.: 15/529,395

(22) PCT Filed: Dec. 1, 2015

(86) PCT No.: PCT/CN2015/096160
§ 371 (c)(1),
(2) Date: May 24, 2017

(87) PCT Pub. No.: WO2017/049763
PCT Pub. Date: Mar. 30, 2017

(65) Prior Publication Data
US 2017/0333053 A1    Nov. 23, 2017

(30) Foreign Application Priority Data

Sep. 21, 2015  (CN) .......................... 2015 1 0604889
Sep. 21, 2015  (CN) ..................... 2015 2 0732833 U

(51) Int. Cl.
B24B 19/22        (2006.01)
A61B 17/16       (2006.01)
(Continued)

(52) U.S. Cl.
CPC .......... A61B 17/1644 (2013.01); A61B 17/16 (2013.01); A61B 17/1626 (2013.01);
(Continued)

(58) Field of Classification Search
CPC .......... B24B 55/02; B24B 55/03; G01K 7/02; G01L 15/00; A61B 2017/1602;
(Continued)

(56) References Cited

U.S. PATENT DOCUMENTS 3,027,625 A * 4/1962 Milstead .............. B23Q 11/141
                                                    184/26
3,131,869 A * 5/1964 Vega ......................... B05B 7/12
                                                    184/55.1
(Continued)

FOREIGN PATENT DOCUMENTS

CN      102858267 A     1/2013
CN      103054624 A     4/2013
(Continued)

OTHER PUBLICATIONS

Jun. 28, 2015 Search Report issued in International Patent Application No. PCT/CN2015/096160.

*Primary Examiner* — George B Nguyen
(74) *Attorney, Agent, or Firm* — Oliff PLC

(57) ABSTRACT

A bone surgery grinding experimental device capable of cooling and electrostatic atomization film formation, including a linear three-axis platform capable of moving front, back, left, right, up and down, an electric spindle and a workpiece fixing device, wherein linear three-axis platform includes an X axis structure capable of carrying out left and (Continued)

right movement, Y axis structure capable of carrying out front and back movement and Z axis structure capable of carrying out up and down movement, the workpiece fixing device is fixed on the Y axis structure, and electric spindle is fixed on the Z axis structure and is installed at workpiece fixing device's upper end; a grinding head is installed at the electric spindle's lower end, a grinding cooling device is arranged inside a grinding head handle or on the grinding head's surrounding, and an electrostatic atomization film formation device is arranged on the grinding head's surrounding.

8 Claims, 13 Drawing Sheets

(51) Int. Cl.
　　　*B24B 55/02*　　　(2006.01)
　　　*G01K 7/02*　　　(2006.01)
　　　*G01L 5/00*　　　(2006.01)
(52) U.S. Cl.
　　　CPC .............. *B24B 19/22* (2013.01); *B24B 55/02* (2013.01); *G01K 7/02* (2013.01); *G01L 5/00* (2013.01); *A61B 2017/1602* (2013.01); *A61B 2017/1651* (2013.01)
(58) Field of Classification Search
　　　CPC ......... B05B 5/03; B05B 5/087; B05B 7/0491; B05B 7/10; H01J 37/32073; H01J 37/3244; H01J 37/32697; H01J 2237/327
　　　USPC .......................................... 451/7, 53, 11, 26
　　　See application file for complete search history.

(56) References Cited

U.S. PATENT DOCUMENTS

| | | | | |
|---|---|---|---|---|
| 3,747,284 A * | 7/1973 | Lyczko | ................... | B24B 55/02 409/136 |
| 3,823,515 A * | 7/1974 | Coes, Jr. | ................... | B24B 1/00 451/53 |
| 3,995,979 A * | 12/1976 | Fedrigo | ................... | B05B 5/08 425/78 |
| 4,129,966 A * | 12/1978 | Smart | ................... | B24B 23/02 451/295 |
| 4,524,543 A * | 6/1985 | Inoue | ................... | B23Q 15/12 451/124 |
| 5,337,963 A * | 8/1994 | Noakes | ................... | B05B 5/0255 239/690 |
| 5,651,834 A * | 7/1997 | Jon | ................... | B08B 7/02 134/26 |
| 5,895,311 A * | 4/1999 | Shiotani | ................... | B23H 1/00 451/11 |
| 6,171,175 B1 * | 1/2001 | Shaikh | ................... | B24B 37/00 451/11 |
| 6,569,099 B1 * | 5/2003 | Babaev | ................... | A61M 3/0275 600/437 |
| 6,669,685 B1 * | 12/2003 | Rizoiu | ................... | A61B 18/20 604/22 |
| 7,090,561 B2 * | 8/2006 | Cambridge | ................... | B24B 47/22 451/11 |
| 7,914,470 B2 * | 3/2011 | Babaev | ................... | A61M 3/0275 128/200.16 |
| 8,257,144 B2 * | 9/2012 | Aoki | ................... | B23P 23/02 451/11 |
| 8,282,027 B2 * | 10/2012 | Suda | ................... | A61L 2/22 134/198 |
| 8,394,461 B2 * | 3/2013 | Komatsubara | ..... | B22D 17/2007 118/629 |
| 2010/0011923 A1* | 1/2010 | Suda | ................... | B23Q 11/10 83/22 |
| 2012/0325436 A1* | 12/2012 | Shedd | ................... | H01L 23/427 165/104.21 |
| 2014/0338709 A1* | 11/2014 | Jewell | ................... | B27K 1/00 134/56 R |
| 2015/0126097 A1* | 5/2015 | Li | ................... | B05B 5/03 451/450 |
| 2015/0362001 A1* | 12/2015 | Nakamura | ................... | B23Q 11/10 137/240 |
| 2016/0120059 A1* | 4/2016 | Shedd | ................... | H05K 7/208 165/244 |

FOREIGN PATENT DOCUMENTS

| | | |
|---|---|---|
| CN | 103072084 A | 5/2013 |
| CN | 103300906 A | 9/2013 |
| CN | 104191376 A | 12/2014 |
| CN | 104257428 A | 1/2015 |
| CN | 204092202 U | 1/2015 |
| CN | 105147356 A | 12/2015 |
| CN | 204971447 U | 1/2016 |

* cited by examiner

BONE SURGERY GRINDING EXPERIMENTAL DEVICE CAPABLE OF COOLING AND ELECTROSTATIC ATOMIZATION FILM FORMATION

FIELD OF THE INVENTION

The present invention relates to the field of medical equipment, and in particular to a bone surgery grinding experimental device capable of cooling and electrostatic atomization film formation.

BACKGROUND OF THE INVENTION

Bone grinding is an essential procedure in neurological surgeries. Clinically, high-speed micro-grinding wheels are commonly used for removing pathological bones. However, high-speed grinding produces a lot of heat, resulting in bone necrosis and heat injury to surrounding tissues, and also has a certain impact on the coagulation function of the tissues, so that normal saline is usually used as cooling fluid to reduce the generation of the heat clinically. The temperature cannot be forecasted in grinding process, so the degree of heat injury cannot be controlled, and grinding heat injury has obtained clinically recognized concern. It is pointed out by Kondo et al. that in the flood cooling mode using normal saline, the maximum temperature generated by the grinding heat would still reach 43° C., and when the maximum temperature is higher than 43° C., optic nerves will be injured and blindness will be caused in serious cases. The maximum temperatures that different parts and different tissues of a human body can born are also different, for example, when the temperature is higher than a critical value 50° C., bones are subjected to different degrees of heat injury, and heat injury to the optic nerves occurs from 43° C. In relation to bone grinding, facial paralysis and femoral head necrosis are also common problems in neurological surgeries. Therefore, in bone grinding, the control of temperature is directly related to the success or failure of the surgeries.

At present, the most commonly used cooling mode in clinic is drip cooling, that is, normal saline is dripped onto a grinding area in a grinding process. When pathological bones needing to be removed by grinding are numerous and when lesions are at parts under wide views, flood cooling can be adopted, that is, a large amount of normal saline is sprayed onto the grinding area to improve the heat transfer capacity of the grinding area. In the machining field, the minimum quantity cooling (MQC) technology is the focus of the current research in grinding processing. However, MQC technology has the shortcoming of insufficient cooling performance, so that its application is greatly limited. A certain proportion of nanoparticles are added into MQC base fluid to improve the heat transfer capacity of a whole jet flow, and meanwhile, the nanoparticle jet minimum quantity cooling (Nano-MQC) for improving the lubrication effect of an oil film in the grinding area emerges. The so-called nanoparticle refers to an ultrafine tinny solid particle of which the size in at least one of the three dimensions is smaller than 100 nm. In Nano-MQC, nanoscale solid particles are added into the grinding fluid, and the nanoparticles, lubricating fluid and compressed air are jetted into the grinding area after mixing and atomization to carry out cooling and lubricating. Based on the solid enhanced heat transfer theory and by means of the advantage that the heat conductivity coefficients of solid particles are much greater than those of fluid and gas, in the same particle volume content, the superficial areas and thermal capacity of the nanoparticles are much greater than those of the millimeter or micron-sized solid particles, and thus the thermal conductivity of nanofluid formed by mixing the nanoparticles with the grinding fluid will be greatly improved.

MQC and Nano-MQC both require special nozzles to atomize cooling fluid or nanofluid, and the traditional atomizing nozzle is a pneumatic atomizing nozzle, that is, the compressed air is fully mixed the cooling fluid or the nanofluid by a gas path and a fluid path so as to be jetted to the grinding area from an outlet of the nozzle in the form of atomized droplets. However, the atomizing effect of the pneumatic atomizing nozzle is not good enough, and the droplets jetted out from the nozzle randomly float in the surrounding air. Jia et al. analyze the advantages and disadvantages of the traditional pneumatic atomizing nozzle, and invent an electrostatic atomizing nozzle, which further atomizes the compressed air and the cooling fluid or the nanofluid on the basis of pneumatic atomization by using the electrostatic atomizing principle, and meanwhile charges the ejected droplets by using the electrostatic charge principle, the charged droplets directionally move towards a workpiece under the action of an electric field force, and thus droplet distribution can be controlled.

Due to high speed rotation of a grinding tool in a bone grinding process, a gas flow barrier hinders the grinding fluid from entering the grinding area effectively. In the drip cooling and the flood cooling, effective cooling fluid capable of entering the grinding area is very little, and the effective flow rates of the MQC and Nano-MQC are very non-ideal. The emergence of the phase change heat transfer technology brings hope for the development of small low-temperature medical equipment. A phase change heat transfer type grinding head consisting of a hollow shaft can be divided into an evaporation segment, a heat insulation segment and a condensation segment, and has a hollow cavity having an initial vacuum degree therein and being filled with a proper amount of working fluid. When the rotating speed is high enough, the working fluid rotates with the grinding head and covers an inner wall surface of the hollow cavity in the grinding head to form an annular fluid film. The grinding area is heated when the grinding head is working, so the working fluid in the grinding area will be evaporated, the fluid film becomes thinner, and the generated steam will flow to the other end of the grinding head. The steam releases heat at the condensation segment to condense into fluid, so that the fluid film is thickened. The condensate returns to a heating end along the inner wall surface under the action of a component force of a centrifugal force. By means of such continuous evaporation, steam flow, condensation and fluid reflux, the heat is transferred from the heating end to the condensation segment. Chen et al. verified the design feasibility and the heat transfer effect of the phase change heat transfer type grinding head by evaluating the isothermal performance, the starting performance and the self heat transfer capacity of the phase change heat transfer type grinding head.

The performance of abrasive grains on the grinding head also has a great impact on the grinding temperature. In order to suppress the heat generated in the grinding area, Toshiyuki carries out grinding experiments on a bovine femur by using an ordinary diamond grinding head, a $SiO_2$ adhered diamond grinding head and a $TiO_2$ adhered diamond grinding head, and finds that compared with the ordinary diamond grinding head, the $SiO_2$ adhered diamond grinding head can slightly reduce the grinding temperature and the grinding torque at the beginning of the grinding, then the grinding temperature exceeds a threshold after a certain period of time, and the same surface load occurs in the grinding like the ordinary diamond grinding head. However, due to the hydrophilicity of micron-sized $TiO_2$ particles, the grinding temperature of the $TiO_2$ adhered diamond grinding head is greatly reduced.

The internal cooling mode is also a common cooling mode in drilling and mechanical grinding processing. In the internal cooling mode, the cooling fluid is directly conveyed to a cutting area through an internal cooling hole of a drill bit or a grinding wheel, so as to effectively reduce the cutting temperature.

Upon research, patent No. ZL201310277636.6 relates to an automatic adjustment type mechanical arm grinding clamping device with six degrees of freedom for medical surgeries, disclosing a technology that has high control accuracy and can effectively avoid the mechanical injury to brain tissues. The mechanical arm grinding clamping device has three rotation and three movement degrees of freedom, namely six degrees of freedom in total, thereby realizing skull surgery operations of arbitrary poses and solve the problems of large working space, high operation difficulty, low operation efficiency and unnecessary additional injury to patients of the traditional handheld operation devices. The device is mainly operated by advanced surgical instruments, and by virtue of the automatic adjustment mechanical arm with six degrees of freedom and the clamping device installed at a front end of the mechanical arm, the device has obvious advantages in aspects of treatment effect, pain reliving ability, recovery period, medical cost and the like. However, the device is not provided with a grinding temperature detection device, so that temperature change in the grinding process cannot be controlled.

Patent No. ZL201310030327.9 relates to an online surgery skull grinding temperature detection and controllable hand-held grinding device, disclosing a technology that monitors an acoustic emission signal of bone grinding to adjust the rotating speed of a grinding wheel and reduce the grinding temperature in the bone grinding process so as to effectively avoid the heat injury to brain tissues. An acoustic emission sensor is arranged at a joint of the grinding wheel and a housing, the acoustic emission signal detected by the acoustic emission sensor during the bone grinding is received by a signal analysis processing module to determine whether an overheating condition occurs, and the rotating speed of a DC motor is controlled by a feedback device. However, sound waves cannot penetrate through the bone tissue and have a significant loss when penetrating through gas-containing tissues, thereby influencing the curative effect. In addition, the device does not monitor the speed and the torque of the grinding wheel in real time, and cannot feed back and control the effective removal condition of pathological bones or the load born by the grinding wheel.

Patent No. ZL201420565334.9 relates to a skull surgery grinding experimental platform with multiple degrees of freedom, including a MQC system, a platform with three degrees of freedom, an electric spindle rotating device, an electric spindle, a grinding force measurement device and a grinding temperature measurement device. The grinding temperature is measured accurately by using three thermocouples distributed in steps, the grinding force is measured by a grinding dynamometer, and guidance is provided for clinical practice by analyzing experimental data. However, in clinical bone grinding surgeries, different surgical areas, different cooling fluid and cooling modes, and the sufficiency of operation experience of doctors will lead to actual and theoretical differences.

The existing invention or device does not consider the treatment on the wound after the bone grinding. When the lesion is located in a wider part, a manual binding mode can be adopted to prevent the infection of the wound. However, when the lesion is at a relatively complex position in the internal structure of human body, in a skull base brain tumor removal surgery for example, because of the complex structure of the skull base and the narrow surgery space, no effective mode is available to treat the wound after the surgery.

SUMMARY OF THE INVENTION

The objective of the present invention is to solve the above-mentioned problems and provide a bone surgery grinding experimental device capable of cooling and electrostatic atomization film formation.

To achieve the above-mentioned objective, the present invention adopts the following technical solutions:

A bone surgery grinding experimental device capable of cooling and electrostatic atomization film formation includes a linear three-axis platform, an electric spindle and a workpiece fixing device, wherein the linear three-axis platform includes an X axis structure capable of carrying out left and right moment, a Y axis structure capable of carrying out front and back movement and a Z axis structure capable of carrying out up and down movement, the workpiece fixing device is fixed on the Y axis structure, and the electric spindle is fixed on the Z axis structure and is installed at an upper end of the workpiece fixing device; a grinding head is installed at a lower end of the electric spindle, a grinding cooling device is arranged inside a grinding head handle or on the surrounding of the grinding head, and an electrostatic atomization film formation device is arranged on the surrounding of the grinding head.

Preferably, the X axis structure is installed on a base, and includes an X axis motor, an X axis speed reducer, an X axis lead screw and an X axis guide rod, the X axis lead screw is connected with the X axis motor through the X axis speed reducer, and the X axis guide rod is arranged to be parallel to the X axis lead screw.

Preferably, the Y axis structure includes a Y axis motor, a Y axis speed reducer, a Y axis lead screw and a Y axis guide rod, the Y axis lead screw is arranged to be perpendicular to the X axis lead screw and is connected with the X axis motor through the X axis speed reducer, and the Y axis guide rod is arranged to be parallel to the Y axis lead screw.

Further preferably, the Z axis structure is installed on the Y axis lead screw and includes a Z axis motor, a Z axis speed reducer, a Z axis lead screw and a Z axis guide rod, the Z axis lead screw is connected with the Z axis motor through the Z axis speed reducer, the Z axis guide rod is arranged to be parallel to the Z axis lead screw, and the electric spindle is installed on the Z axis lead screw.

Preferably, the grinding experimental device includes a workpiece grinding temperature monitoring system, the workpiece grinding temperature monitoring system includes a thermocouple and a thermocouple data collector, which are connected with each another, the thermocouple penetrates through a workpiece from bottom to top and is flush with an upper surface of the workpiece, the thermocouple data collector is connected with a control system, and the control system is connected with the grinding cooling device.

Preferably, the grinding experimental device includes a force measurement system, the force measurement system includes a force measurement device and a force measurement instrument data collector, which are connected with each another, and the force measurement instrument data collector is connected with the control system. Further preferably, the force measurement device includes a workpiece fixing device and two force measurement instruments that are respectively installed at both ends of the workpiece fixing device, and the force measurement instruments are connected with the force measurement instrument data collector. The force measurement device can detect the signal of grinding forces.

Preferably, the workpiece fixing device includes a workpiece chamber, a plurality of upper pressure plates used for fixing the workpiece from the upper side and a side face extrusion device used for fixing the workpiece from the side face, and the upper pressure plates and the side face extrusion device both are installed on a side wall of the workpiece chamber.

Preferably, the grinding cooling device is a drip cooling device, a flood cooling device, a Nano-MQC, a phase change heat transfer cooling device or an electrostatic atomization internal cooling device.

Further preferably, the drip cooling device and the flood cooling device have the same structure and each include a fluid storage tank, a hydraulic pump, a pressure regulating valve, a throttle valve and a nozzle, which are connected in sequence, and the nozzle is installed on the surrounding of the grinding head.

Further preferably, the drip cooling device and the flood cooling device further each include an overflow valve and a recycling bin, which are connected with each another, and the overflow valve communicates with a pipeline between the pressure regulating valve and the throttle valve.

Preferably, the Nano-MQC device includes a nozzle, a gas flow path and a fluid flow path, the gas flow path includes an air compressor, a gas storage tank, a gas pressure regulating valve, a gas throttle valve and a gas flowmeter, which are connected in sequence, the fluid flow path includes a fluid storage tank, a hydraulic pump, a fluid pressure regulating valve, a fluid throttle valve and a fluid flowmeter, which are connected in sequence, and the fluid flowmeter and the gas flowmeter are both connected with the nozzle.

The used cooling fluid is nanofluid prepared from normal saline and nanoparticles, and in addition, the principle and the design are the same as those in the third embodiment. The nanoparticles can adopt hydroxyapatite, which is the main inorganic component of bones and teeth of human and animals, has excellent biocompatibility and biological activity, and can be closely combined with soft and hard tissues of human body after being implanted in the human body, thereby being a widely used bone graft substitute. After hydroxyapatite is implanted into a human bone, bone cells and collagen fibers grow in the internal pores therein, the strength and stiffness of hydroxyapatite will gradually increase, and hydroxyapatite ultimately becomes a part of the living bone. Studies show that hydroxyapatite nanoparticles have different degrees of inhibiting effects on the growth of liver cancer, gastric cancer, osteosarcoma and other cancer cells. Therefore, in a bone grinding process, the cooling fluid containing the hydroxyapatite nanoparticles is sprayed to a contact area of a lesion and the grinding tool to ensure the absolute safety to the human body at first, and a role of auxiliary cooling can also be played as its thermal conductivity coefficient is higher than those of gas and fluid. After a surgical process is terminated, the hydroxyapatite naturally degrades in the human body, and the secondary generation of tumors can also be prevented due to the inhibition of the hydroxyapatite to the growth of cancer cells.

Further preferably, an anti-overload equipment component is further connected to the fluid flow path, the anti-overload equipment component includes an overflow valve and a recycling bin, which are connected with each another, and the overflow valve communicates with a pipeline between the fluid throttle valve and the fluid pressure regulating valve.

Further preferably, the nozzle includes a fluid inlet, a gas passage and a gas-fluid mixing passage, the gas-fluid mixing passage is arranged along an axial direction of the nozzle, the gas passage is annularly arranged around a fluid passage, the gas passage communicates with the gas flow path through a gas outlet, and both of the fluid inlet and the gas passage communicates with the gas-fluid mixing passage.

Further preferably, the gas-fluid mixing passage includes a mixing segment, an acceleration segment and a swirl chamber, which communicate with one another in sequence, the mixing segment communicates with the fluid inlet and the gas passage separately, the acceleration segment is conical, an open end is connected with the mixing segment, a necking end is connected with the swirl chamber, and an outlet end of the swirl chamber is necking down.

Preferably, the phase change heat transfer cooling device is hollow, a hollow cavity is filled with condensate, the phase change heat transfer cooling device includes an evaporation segment, a heat insulation segment and a condensation segment, the interior of the hollow cavity is vacuumized, the condensate evaporates at the evaporation segment and condenses at the condensation segment to dissipate heat, and the process is circulated.

Preferably, the grinding head is a phase change heat transfer grinding head, a hydrophilic grinding head or an electrostatic atomization internal cooling grinding head.

Further preferably, the phase change heat transfer cooling device is installed in a grinding head handle of the phase change heat transfer grinding head, the evaporation segment is installed close to the grinding head, the condensation segment is installed away from the grinding head, the condensation segment is provided with cooling fins, and an inner taper angle of the evaporation segment is smaller than 90°.

When the rotating speed is high enough, nanofluid rotates with the grinding head and covers an inner wall surface of the hollow cavity in the grinding head to form an annular fluid film. When the grinding head is working, the grinding area is heated, the nanofluid base fluid in the grinding area will be evaporated, the fluid film becomes thinner, and the generated steam will flow to the other segment of the hollow cavity in the grinding head. The steam releases heat at the condensation segment and condenses into fluid, so that the fluid film is thickened. The condensate returns to a heating segment along the inner wall surface under the action of a component force of a centrifugal force. By means of such continuous evaporation, steam flow, condensation and fluid reflux, the heat is transferred from the heating segment to the condensation segment. The inner taper angle a of the hollow cavity in the nanofluid phase change heat transfer grinding head plays a turbulent flow role on the nanofluid to break the formation or sufficient development of a boundary layer on one hand so as to reinforce the heat transfer, and realizes the reflux of the nanofluid base fluid on the other hand.

Further preferably, abrasive grains and micron-sized $TiO_2$ are attached to the hydrophilic grinding head, the abrasive grains are uniformly distributed on the grinding head, and the micron-sized $TiO_2$ is distributed on the surrounding of the abrasive grains. Due to the hydrophilia of the micron-sized $TiO_2$, the cooling fluid can be attached to the abrasive grains in the grinding process more easily, thereby effectively reinforcing the heat dissipation of the grinding area.

Further preferably, the electrostatic atomization internal cooling grinding head includes a Mohs spindle, an electrostatic atomization film formation structure and an electrostatic atomization internal cooling grinding structure, the electrostatic atomization film formation structure sleeves on an outer side of the electrostatic atomization internal cooling grinding structure, a jet orifice of the electrostatic atomization film formation structure is arranged to face to the grinding head.

Further preferably, a fixedly arranged fixing jacket sleeves on the Mohs spindle.

Further preferably, the Mohs spindle is connected with the fixing jacket through a tapered roller bearing component.

In an actual operation, the grinding device and the horizontal plane form a certain angle, so the internal cooling grinding head handle needs to bear forces in two directions: the axial direction and the radial direction, then the Mohs spindle also needs to bear the forces in two directions: the axial direction and the radial direction, therefore the device adopts tapered roller bearings, and two tapered roller bearings are located by an end cover and a sleeve as well as by the fixing jacket and the sleeve respectively. Both ends of the hearings are sealed by, sealing rings to prevent leakage of lubricating oil. The end cover is fixed on the fixing jacket by a screw and a gasket, and the gasket can adjust the gaps and backlashes of the bearings and the axial position of the spindle.

Further preferably, the electrostatic atomization internal cooling grinding structure includes a grinding head, a conducting wire connecting block, a high voltage conversion device and a power supply, the grinding head handle of the grinding head is fixed in the Mohs spindle, the conducting wire connecting block is fixed to the Mohs spindle, the high voltage conversion device sleeves on the outer side of the grinding head handle and is fixedly arranged, the conducting wire connecting block is movably connected with the high voltage conversion device, the high voltage conversion device is connected with the power supply, an internal cooling hole is formed in the grinding head handle, the internal cooling hole penetrates through the grinding head and the grinding head handle, and the conducting wire connecting block is connected with the internal cooling hole through a conducting wire.

Further preferably, the internal cooling hole is a double-helical pore passage. Compressed air, the cooling fluid or the nanofluid is directly sprayed to the grinding area after being accelerated in two helical holes in the grinding process, so that the temperature in the grinding area can be effectively reduced, and the grindings are brushed away, so that the service life of a cutter is prolonged.

Further preferably, a grinding head handle clamping body is arranged on the Mohs spindle, and the grinding head handle is installed inside the grinding head handle clamping body.

The Mohs spindle rotates and drives the grinding head handle clamping body to rotate, and the high voltage conversion device is fixed on the fixing jacket and is static. A roller is integrated with the conducting wire connecting block and rotates in an inner groove of the high voltage conversion device, so that high voltage is transferred from a fixed high-voltage outer conducting wire to a rotary high-voltage inner conducting wire. Due to a low corona inception voltage of negative corona discharge during corona discharge and a high breakdown voltage, the high voltage conversion device can be connected with the negative electrode of an adjustable high-voltage DC power supply to charge the fluid.

Further preferably, the electrostatic atomization film formation structure includes an injection pump, an electrode disc installed to fit the inner wall of the injection pump, an electrode component fixed on the electrode disc and a jet orifice formed in an outlet end of the injection pump, the electrode component and a workpiece powering device are respectively connected with the negative electrode and the positive electrode of an electrostatic generator, a plunger of the injection pump is connected with a motor, and the jet orifice is vertically formed and is formed to incline toward the grinding head.

Further preferably, the plunger of the injection pump is hermetically arranged.

The electrostatic atomization film formation structure is a device for atomizing a spinning medium into droplets, and finally curing the droplets into fibers and forming a film.

A pressure cavity composed of the injection pump and the plunger of the electrostatic atomization film formation structure is filled with medical dressings, the plunger is connected with the motor through a conducting wire placement groove, and a sealing ring is arranged on an outer circle of the plunger. The electrode disc is arranged at a bottom end of the injection pump, and the electrode disc is fixed on the injection pump by four screws. The electrode disc is connected with the negative electrode of the high voltage electrostatic generator by two electrodes through the conducting wire placement groove so as to charge the fluid. An electrostatic spinning structure is adjusted to a proper height, after the control system gives a movement instruction, the plunger moves downward to provide a continuous and constant thrust for a pressure cavity, the medical dressings are extruded onto the jet orifice at a fixed rate, and the medical dressings form droplets under the synergistic effect of the gravity, the viscosity and the surface tension thereof, and the droplets are suspended on the jet orifice. The external voltage is adjusted to a proper voltage, so that the droplets are jetted out from the jet orifice in the form of jet flow. When the jet flow is stretched to a certain extent, the jet flow will bend and generate a further split stretch phenomenon, and as the specific surface area of the jet flow increases quickly at the moment, the solvent is quickly volatilized, and finally is collected on a collection net and cured into a non-woven-shaped fibrofelt. The device can be provided with one or more jet orifices. In the actual operation, an indicator lamp faces to a grinding feed direction, namely fibers jetted out from the jet orifice drop onto a ground wound.

In the electrostatic atomization structure, two conducting wires of the conducting wire connecting block stretch into the internal cooling hole of the internal cooling grinding head handle. The Mohs spindle rotates and drives the grinding head handle clamping body to rotate by a flat key, and the high voltage conversion device is fixed on the fixing jacket by the gasket and screws and is static. The roller is integrated with the conducting wire connecting block and rotates in the inner groove of the high voltage conversion device, so that high voltage is transferred from the fixed high-voltage outer conducting wire to the rotary high-voltage inner conducting wire. The high voltage conversion device can be connected with the negative electrode of the adjustable high-voltage DC power supply through the conducting wire placement groove and conducting wires to charge the fluid. The positive electrode of the adjustable high-voltage DC power supply is connected with the workpiece powering device and is grounded by a grounding wire.

Further preferably, the electrostatic atomization internal cooling grinding head further includes a telescopic sleeve structure, the telescopic sleeve structure includes a hand rotating sleeve and a push plate, the hand rotating sleeve is movably installed on the fixing jacket, the hand rotating sleeve is in threaded connection with the push plate, a groove for clamping the push plate is formed in the fixing jacket, an elastic medium, preferably a spring, is arranged between the push plate and the fixing jacket in the groove, the injection pump is connected with the push plate, and the push plate is of an integral structure or a split structure.

Further preferably, the push plate is of the split structure and includes a push plate body and a push plate connecting block, the push plate body is in threaded connection with the hand rotating sleeve, the push plate body is connected with the push plate connecting block, a groove for clamping the push plate connecting block is formed in the fixing jacket, and an elastic medium, preferably a spring, is arranged between the push plate and the fixing jacket in the groove.

Further preferably, the push plate body is connected with the push plate connecting block through a ball, and the ball is located in a channel formed by the hand rotating sleeve and the fixing jacket.

The working principle of the telescopic sleeve structure is as follows:

The hand rotating sleeve is fixed on the fixing jacket through the groove in the fixing jacket, and the push plate is in threaded connection with the hand rotating sleeve. Anti-skid stripes are arranged on the outer surface of the hand rotating sleeve to prevent the hand rotating sleeve from skidding when the same is rotated. If the hand rotating sleeve is rotated clockwise, the push plate will move downward through the threaded connection to push the ball to roll downward, and then the ball pushes the push plate and the push plate connecting block to move downward in sequence. The push plate connecting block is connected with the injection pump by a screw, thereby pushing the injection pump to move downward. Since the fixing jacket is fixed in the up and down direction, when the push plate connecting block moves downward, the spring will be compressed. If the hand rotating sleeve is rotated counterclockwise, the pressure applied to the spring is reduced, the spring extends out and sequentially pushes the push plate connecting block, the push plate and the ball to move or roll upward. Therefore the extension and retraction of the sleeve structure are realized.

The present invention has the following beneficial effects:

1. The high-speeding grinding surgery experimental device of the present invention can be applicable to drip cooling, flood cooling, MQC, Nano-MQC, the phase change heat transfer grinding head, the hydrophilic grinding head, the electrostatic atomization internal cooling grinding tool and other modes in which the temperature of the grinding area is reduced, and guidance is provided for clinical practice by experimental measurement and theoretical analysis;

2. the experimental platform of the present invention can adjust the position of the workpiece front and back, and adjust the position of the grinding head left and right, and up and down to adapt to the grinding of workpieces with different sizes;

3. the force measurement system and the temperature monitoring system are further arranged on the experimental device of the present invention, so that the grinding power can be reasonably controlled and the cooling mode can be reasonably selected by monitoring the grinding force and the grinding temperature in the grinding process; and 4. the electrostatic atomization internal cooling grinding head of the present invention is an integrated device of an electrostatic atomization internal cooling grinding tool and an electrostatic atomization film formation device, the electrostatic atomization internal cooling grinding tool and the electrostatic atomization film formation device are of a sleeve structure, thereby being not only able to fully atomize the cooling fluid and control the distribution of droplets of the cooling fluid to effectively reduce the temperature in the grinding area, but also able to jet the medical dressings to the wound surface after grinding in time by the electrostatic atomization film formation device while performing the bone grinding, in order to promote wound healing and prevent infection.

REFERENCE SIGNS

Figure 1:
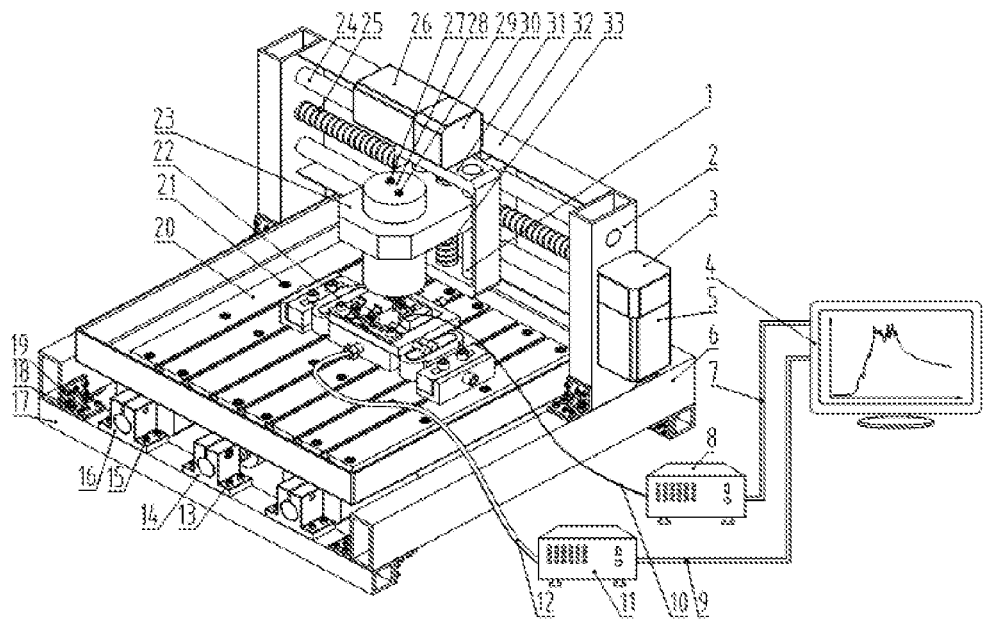
FIG. 1 is an isometric diagram of a high-speed grinding surgery experimental platform.

1—Z axis guide rod, 2—vertical rod guide rail, 3—X axis speed reducer, 4—control system, 5—X axis motor, 6—base I, 7—data connecting line I, 8—thermocouple data collector, 9—data connecting line II; 10—thermocouple, 11—force measurement instrument data collector, 12—force measurement instrument signal transmission line, 13—screw I, 14—Y axis lead screw seat, 15—screw II, 16—Y axis guide rod seat, 17—base II, 18—screw III, 19—corner connecting piece, 20—working table I, 21—working table bolt, 22—force measurement instrument I, 23—electric spindle fixture, 24—X axis guide rod, 25—X axis lead screw, 26—Z axis motor, 27—electric spindle cooling fluid inlet, 28—electric spindle, 29—electric spindle cooling fluid outlet, 30—Z axis speed reducer, 31—X axis protection box, 32—protection box, 33—Z axis lead screw, 34—Y axis motor, 35—Y axis speed reducer, 36—Y axis lead screw, 37—Y axis guide rod, 38—grinding head I, 39—bone test sample, 40—annular block, 41—screw IV, 42—screw V, 43—force measurement instrument base, 44—screw VI, 45—flat plate I, 46—pressure plate, 47—bolt I, 48—nut I, 49—gasket I, 50—screw VII, 51—flat plate II, 52—stop dog, 53—screw VIII, 54—throttle valve I, 55—pressure regulating valve I, 56—hydraulic pump I, 57—fluid storage tank I, 58—overflow valve I, 59—recycling bin I, 60—turbine flowmeter I, 61—throttle valve II, 62—turbine flowmeter II, 63—throttle valve III, 64—pressure regulating valve II, 65—gas storage tank, 66—pressure gauge, 67—filter, 68—air compressor, 69—pressure regulating valve III, 70—hydraulic pump II, 71—fluid storage tank II, 72—overflow valve II, 73—recycling bin II, 74—liquid injection channel joint, 75—gas injection channel joint, 76—gas hole, 77—nozzle body, 78—swirl chamber, 79—acceleration chamber, 80—gas hole wall, 81—mixing chamber, 82—grinding head handle I, 83—bolt II, 84—nut II, 85—sleeve I, 86—sleeve II, 87—grinding head matrix, 88—conical cylinder, 89—abrasive grain I, 90—cooling fin I, 91—cooling fin II, 92—cooling fin III, 93—gasket II, 94—twisting gasket, 95—external reinforcement ring, 96—filler, 97—internal reinforcement ring, 98—grinding head handle II, 99—grinding head II, 100—abrasive grain II, 101, micron-sized $TiO_2$, 102—high voltage electrostatic generator, 103—injection pump I, 104—spinning medium I, 105—metal electrode, 106—jet flow, 107—receiving plate, 108—Mohs spindle, 109—sealing ring I, 110—screw IX, 111—gasket III, 112—tapered roller bearing I, 113—screw III, 114—rotary sealing ring I, 115—fixing jacket, 116—rotary sealing ring II, 117—hand rotating sleeve, 118—push plate I, 119—sleeve IV, 120—ball, 121—tapered roller bearing II, 122—push plate II, 123—sealing ring II, 124—spring, 125—injection pump II, 126—internal cooling hole, 127—chuck, 128—locking nut, 129—adjustable high voltage DC power supply, 130—workpiece powering device, 131—working table II, 132—force measurement instrument II, 133—workpiece, 134—internal cooling grinding head, 135—indicator lamp, 136—internal cooling grinding head handle, 137—rotary sealing ring III, 138—antiskid stripe, 139—locating axis, 140—gasket IV, 141—end cover, 142—push plate connecting block, 143—screw X, 144—conducting wire placement groove I, 145—conducting wire I, 146—grounding wire, 147—conducting wire placement groove II, 148—jet orifice, 149—spinning medium II, 150—electrode, 151—electrode disc, 152—sealing ring III, 153—plunger, 154—screw XI, 155—flat key, 156—conducting wire II, 157—conducting wire placement groove III, 158—grinding head handle clamping body, 159—conducting wire III, 160—conducting wire IV, 161—gasket V, 162—screw XII, 163—gasket VI, 164—screw XIII, 165—conducting wire connecting block, 166—roller, 167—high voltage conversion device, 168—pressure cavity, 169—horizontal hole, 170—vertical hole, and 171—cooling fluid inlet.

DETAILED DESCRIPTION OF THE EMBODIMENTS

Seven embodiments of the present invention will be illustrated below in detail in combination with the accompany drawings.

Figure 2:
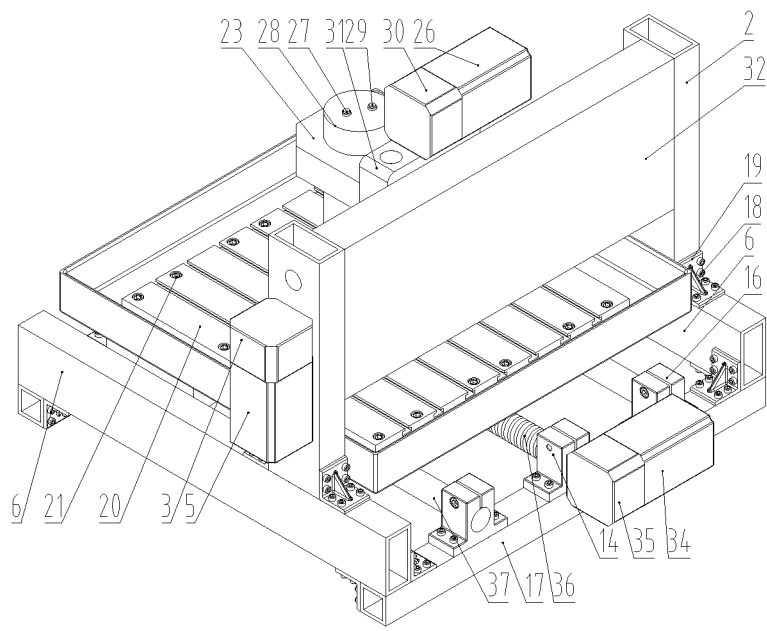
FIG. 2 is an isometric diagram of a linear three-axis platform.

All embodiments of the present invention are implemented on a high-speed grinding surgery experimental platform as shown in FIG. 1. The experimental platform is mainly composed of a linear three-axis platform (as shown in FIG. 2), an electric spindle 28, a force measurement instruction I 22, a thermocouple 10 and a control system 4. The linear three-axis platform includes an X axis structure, a Y axis structure and a Z axis structure. The X axis structure is composed of an X axis motor 5, an X axis speed reducer 3, an X axis lead screw 25, an X axis guide rod 24 and an X axis protection box 31, and the X axis lead screw 25 is connected with the X axis motor 5 through the X axis speed reducer 3; one or two X axis guide rods 24 are provided, and the X axis guide rod(s) 24 is(are) arranged to be parallel to the X axis lead screw 25. When there are two X axis guide rods 24, the two X axis guide rods 24 are respectively arranged on both sides of the X axis lead screw 25 in parallel. The Y axis structure is composed of a Y axis motor 34, a Y axis speed reducer 35, a Y axis lead screw 36, a Y axis lead screw seat 14, a screw I 13, a Y axis guide rod 37, a Y axis guide rod seat 16 and a screw II 15; and the Z axis structure is composed of a Z axis motor 26, a Z axis speed reducer 30, a Z axis lead screw 33, a Z axis guide rod 1 and an electric spindle fixture 23.

Figure 3:
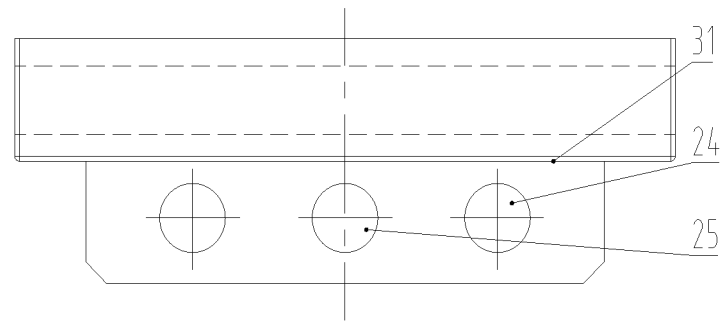
FIG. 3 is a front view of an X axis protection box.
Figure 4:
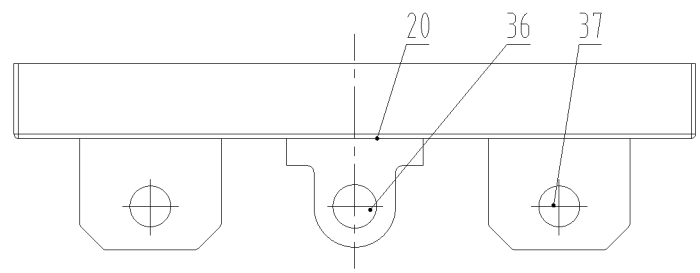
FIG. 4 is a front view of a working table.
Figure 5:
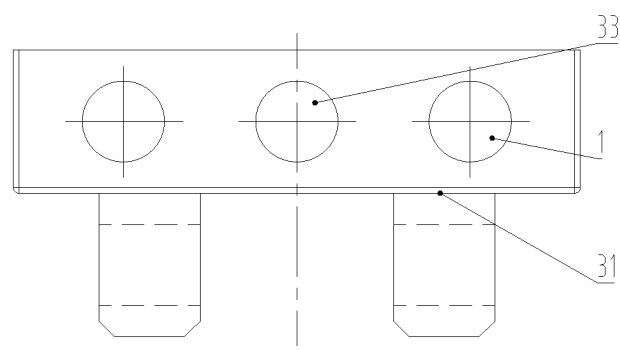
FIG. 5 is a side view of an X axis structure protection box.

After the control system 4 sends an X axis movement instruction, the X axis motor 5 is powered on to run and drives the X axis lead screw 25 to run after being decelerated by the X axis speed reducer 3. The X axis lead screw 25 and the X axis guide rod 24 are respectively concentric to a through hole in a bottom surface of the X axis protection box 31 (as shown in FIG. 3), and both ends of the X axis lead screw 25 and the X axis guide rod 24 are respectively installed in the through hole of the vertical rod guide rail 2. The X axis lead screw 25 drives the X axis protection box 31 to carry out translation along the X axis direction while rotating, and the X axis guide rod 24 can prevent the X axis protection box 31 from skewing. The Y axis lead screw 36 and the Y axis guide rod 37 are respectively installed in the through hole in the bottom surface of a working table I 20 (as shown in FIG. 4), and the Z axis lead screw 33 and the Z axis guide rod 1 are respectively installed in through holes in upper and lower ends of the X axis protection box 31 (as shown in FIG. 5).

The movement mechanisms of the Y axis and the Z axis are the same as that of the X axis, the movement mechanism of the Y axis is as follows: the Y axis motor 34 is started and is decelerated by the Y axis speed reducer 35 to drive the Y axis lead screw 36 to rotate, so as to drive the working table I 20 to carry out translation along the Y axis lead screw 36. The movement mechanism of the Z axis is as follows: the Z axis motor 26 is started and is decelerated by the Z axis speed reducer 30 to drive the Z axis lead screw 33 to rotate, so as to drive the electric spindle fixture 23 to carry out translation along the Z axis lead screw 33. Both ends of the Y axis lead screw 36 are fixed on a base II 17 by the Y axis lead screw seat 14 and the screw I 13, and both ends of the Y axis guide rod 37 are fixed on the base II 17 by the Y axis guide rod seat 16 and the screw II 15. The base I 6 and the base II 17 are connected and fixed by a corner connecting piece 19 and a screw III 18, and the base I 6 is installed at an upper end of the base II 17. A protection box 32 can prevent the damage of dust and scrap iron to the linear three-axis platform so as to prolong the service thereof and bring sense of beauty to the linear three-axis platform. When a workpiece having no magnetism needs to be installed on the working table I 20, the workpiece is fixed by a working table bolt 21 through a special fixture.

Figure 6:
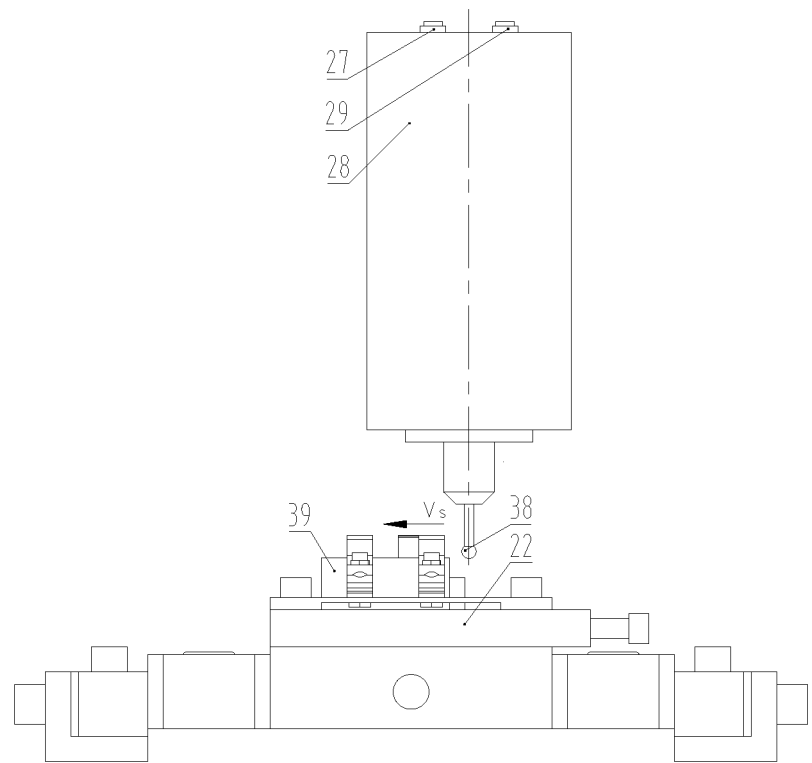
FIG. 6 is a front view of installation positions of an electric spindle and a force measurement instrument.
Figure 7:
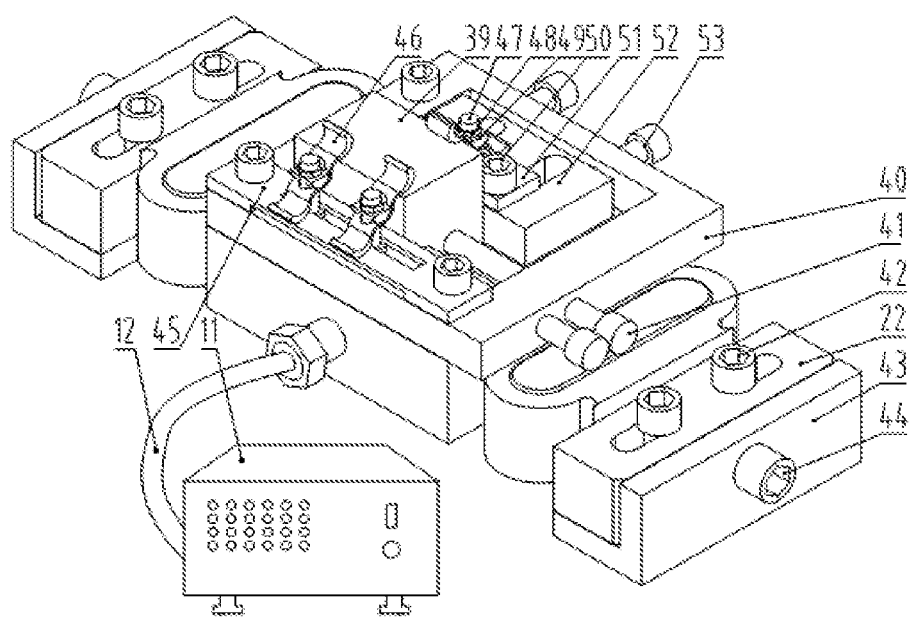
FIG. 7 is an isometric diagram of the force measurement instrument.

FIG. 6 shows a front view of installation positions of an electric spindle 28 and a force measurement instrument I 22. A grinding head I 38 is clamped on the electric spindle 28, and the center line of the electric spindle 28 is perpendicular to a to-be-ground surface of a bone test sample 39. The cooling mode of the electric spindle 28 is water cooling, and the cooling fluid is injected from an electric spindle cooling fluid inlet 27 and flows out from an electric spindle cooling fluid outlet 29 after the circulation inside the electric spindle 28. The clamping mode of the bone test sample 39 on the force measurement instrument I 22 is as shown in FIG. 7. The grinding force measurement instrument I 22 is fixed by front and back force measurement instrument bases 43 and is clamped by a screw V 42 and a screw VI 44, and the two bases 43 are made of a magnetizable metal. After the working table I 20 of the platform with three degrees of freedom is opened, the working table I 20 is magnetized to absorb the bases 43 of the grinding force measurement instrument I 22 on the working table I 20. An annular block 40 is fixed to the working table of the grinding force measurement instrument I 22, the bone test sample 39 is placed on the working table of the grinding force measurement instrument I 22, and the six degrees of freedom of the bone test sample 39 can be completely located by the annular block 40 and the working table of the grinding force measurement instrument I 22. The Y axis direction of the bone test sample 39 is clamped by using two screws VIII 53, and the X axis direction of the bone test sample is clamped by using a screw IV 41. One face of a stop dog 52 is in contact with the side of the bone test sample 39, one face thereof is in contact with the two screws VIII 53, and the screws VIII 53 are screwed down to clamp the stop dog 52 in the Y direction of the bone test sample 39. The bone test sample 39 is clamped by three pressure plates 46 in the Z direction, and the three pressure plates 46 constitute a self-regulating pressure plate by means of a flat plate I 45, a flat plate II 51, a gasket I 49, a bolt I 47 and a nut I 48, and the flat plate II 51 is fixed to the stop dog 52 by a screw VII 50. When three sizes, namely length, width and height, of the bone test sample 39 change, the equipment can be regulated by two screws IV 41, two screws VIII 53 and three pressure plates 46 so as to meet the size change requirements of the bone test sample 39. The stop dog 52 is clamped by the screw VII 50 and the screws VIII 53. When the bone test sample 39 is subjected to a grinding force, a measurement signal is transmitted to a force measurement instrument data collector 11 by a force measurement instrument signal transmission line 12 and is transmitted to the control system 4 by a data connecting line II 9, and the magnitude of the grinding force is displayed.

Figure 8:
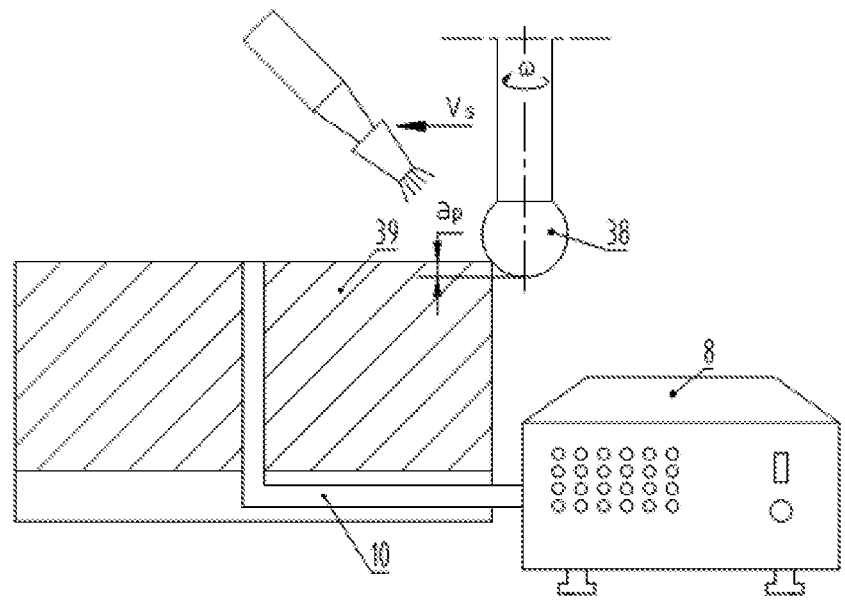
FIG. 8 is a schematic diagram of installation of a temperature measurement device.

FIG. 8 shows a schematic diagram of installation of a temperature measurement device. A hole is drilled in the center of the bone test sample 39 and a groove is formed by lathing in the bottom face thereof to lead out the thermocouple 10. The top end of the thermocouple 10 is flush with the to-be-ground surface of the bone test sample 39. When a grinding head I 38 grinds the thermocouple at an angular velocity $\omega$, a feed rate $v_s$ and a grinding depth $a_p$, the length of the $a_p$ segment at the top of the thermocouple 10 is removed, the measurement signal is transmitted by a thermocouple data collector 8 and a data connecting line I 7 to the control system 4, and a measured temperature is displayed. Therefore a bone grinding temperature can be obtained.

Figure 9:
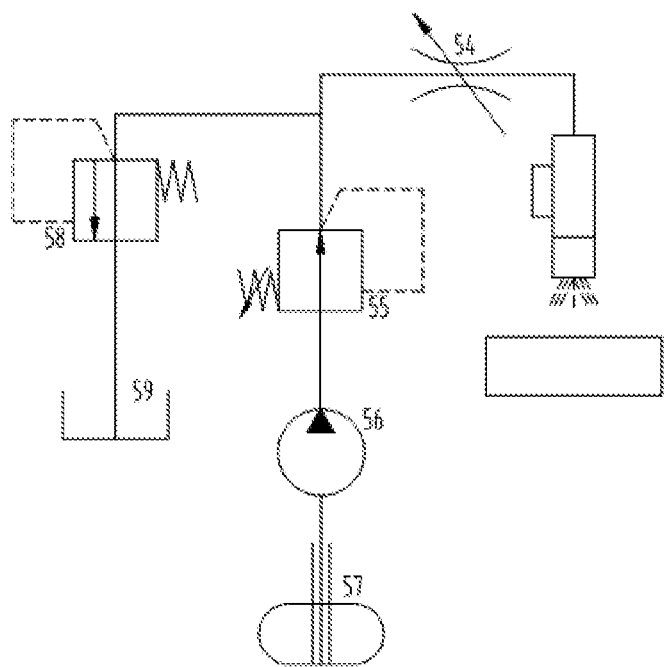
FIG. 9 is a diagram of a fluid path system in first and second embodiments.

The first embodiment of the present invention is as shown in FIG. 9, and FIG. 9 is a diagram of a fluid path system in a commonly used drip cooling mode in clinical orthopaedic grinding surgeries. As shown in FIG. 9, the fluid path is composed of a fluid storage tank I 57, a hydraulic pump I 56, a pressure regulating valve I 55 and a throttle valve I 54, which are connected in sequence. The fluid storage tank I 57 is filled with normal saline, the normal saline in the fluid storage tank I 57 is pumped out by the hydraulic pump I 56 and enters the nozzle through the pressure regulating valve I 55 and the throttle valve I 54. An overflow valve I 58 and a recycling bin I 59 form a protection path. As the flow velocity of the cooling fluid in the drip cooling mode is very low, the hydraulic pump I 56 is a variable frequency water pump, and the flow thereof can be controlled by regulating the pressure to obtain an ideal flow velocity.

The second embodiment of the present invention is flood cooling, the flow velocity of the cooling fluid thereof is much higher than that in the drip cooling mode, and except that the pressure of the hydraulic pump is different from that in the first embodiment, other designs are the same as those in the first embodiment.

Figure 10:
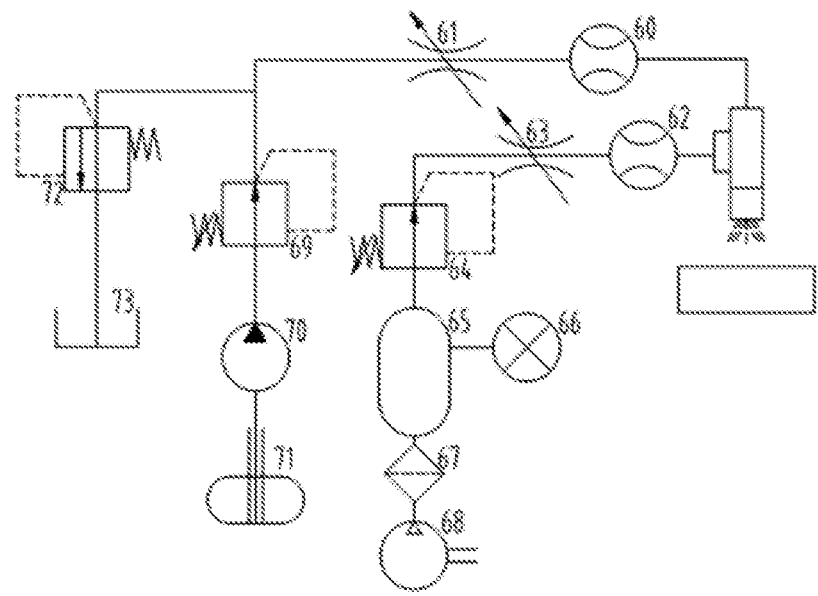
FIG. 10 is a diagram of fluid path and gas path systems in third and fourth embodiments.
Figure 11:
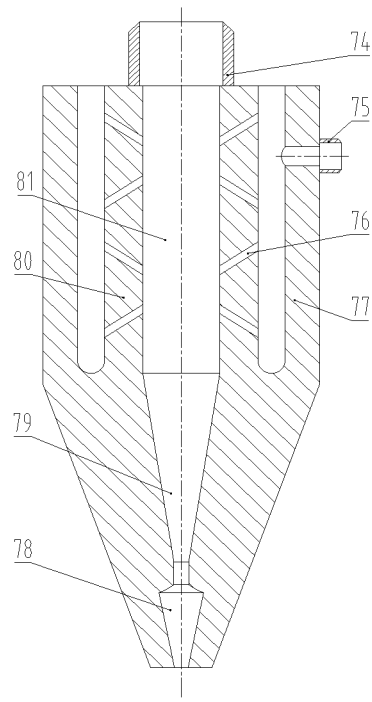
FIG. 11 is a sectional view of third and fourth embodiments.

The third embodiment of the present invention is MQC, and the used nozzle is a pneumatic atomizing nozzle. FIG. 10 is a diagram of fluid path and gas path systems, and the principle of the MQC can be illustrated in combination with FIG. 11, and involves a fluid path, a gas path and the nozzle. As shown in FIG. 10, a fluid storage tank II 71 is filled with normal saline, and high pressure gas and the normal saline are mixed in a nozzle body 77 (FIG. 11). The gas path is composed of an air compressor 68, a filter 67, a gas storage tank 65, a pressure regulating valve II 64, a throttle valve III 63 and a turbine flowmeter II 62, which are connected in sequence, and the fluid path is composed of the fluid storage tank II 71, a hydraulic pump II 70, a pressure regulating valve III 69, a throttle valve II 61 and a turbine flowmeter I 60, which are connected in sequence. During working, the hydraulic pump II 70 is started, the normal saline stored in the fluid storage tank II 71 enters a fluid injection channel joint 74 of the nozzle through the fluid pressure regulating valve III 69, the fluid throttle valve II 61 and the turbine flowmeter I 60. An overflow valve II 72 acts as a safety valve, and the overflow valve II 72 is opened when the pressure in the fluid path exceeds a set pressure, so that the normal saline returns into a recycling bin II 73 through the overflow valve II 72. While the overflow valve II 72 is started, the air compressor 68 is started, high pressure gas enters a gas injection channel joint 75 of the nozzle through the filter 67, the gas storage tank 65, the gas pressure regulating valve II 64, the gas throttle valve III 63 and the turbine flowmeter II 62, and a pressure gauge 66 monitors the pressure value in the gas path. The high pressure gas enters a mixing chamber 81 through gas holes 76 distributed in a gas hole wall 80, is fully mixed and atomized with the normal saline from the fluid injection channel joint 74 in the nozzle mixing chamber 81 and enters a swirl chamber 78 after being accelerated in an acceleration chamber 79, so that the high pressure gas and the normal saline are further mixed and accelerated and are sprayed to the grinding area from the nozzle outlet in the form of atomized droplets. An optimal MQC effect can be achieved by regulating the pressure regulating valves, the throttle valves and the flowmeters in the gas path and the fluid path, and by regulating the pressure and the flow of the high pressure gas.

The fourth embodiment of the present invention is Nano-MQC. The used cooling fluid is nanofluid prepared from normal saline and nanoparticles, and the principle and design thereof are the same as those in the third embodiment. The nanoparticles can adopt hydroxyapatite, which is the main inorganic component of bones and teeth of human and animals, has excellent biocompatibility and biological activity, and can be closely combined with soft and hard tissues of human body after being implanted in the human body, thereby being a widely used bone graft substitute. After hydroxyapatite is implanted into a human bone, bone cells and collagen fibers grow in the internal pores therein, the strength and stiffness of hydroxyapatite will gradually increase, and ultimately hydroxyapatite becomes a part of the living bone. Studies show that hydroxyapatite nanoparticles have different degrees of inhibiting effects on the growth of liver cancer, gastric cancer, osteosarcoma and other cancer cells. Therefore, in a bone grinding process, the cooling fluid containing the hydroxyapatite nanoparticles is sprayed to a contact area of a lesion and the grinding tool to ensure the absolute safety to the human body at first, and a role of auxiliary cooling can also be played as its thermal conductivity coefficient is higher than those of gas and fluid. After a surgical process is terminated, the hydroxyapatite naturally degrades in the human body, and the secondary generation of tumors can also be prevented due to the inhibition of the hydroxyapatite to the growth of cancer cells.

Figure 12:
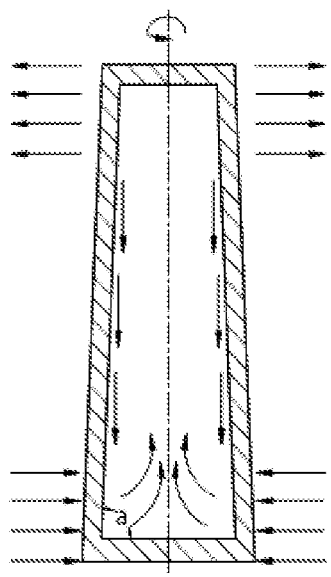
FIG. 12 is a working principle diagram of a fifth embodiment.
Figure 13:
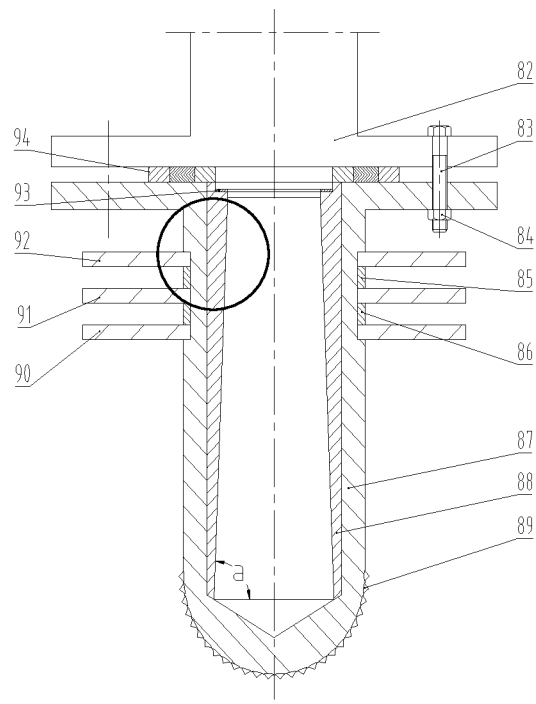
FIG. 13 is a sectional view of the fifth embodiment.
Figure 14:
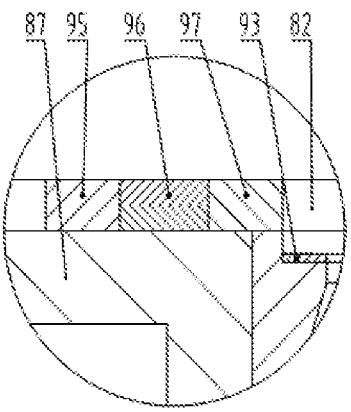
FIG. 14 is an enlarged drawing of a sealing structure of the fifth embodiment.

The fifth embodiment of the present invention is a nanofluid phase change heat transfer grinding head, and FIG. 12 is a working principle diagram thereof. As shown in the figure, the nanofluid phase change heat transfer grinding head consists of a hollow shaft, and can be divided into an evaporation segment, a heat insulation segment and a condensation segment, and has a hollow cavity having an initial vacuum degree therein and being filled with a proper amount of nanofluid. When the rotating speed is high enough, the nanofluid rotates with the grinding head and covers an inner wall surface of the hollow cavity in the grinding head to form an annular fluid film. The grinding area is heated when the grinding head is working, so the nanofluid base fluid in the grinding area will be evaporated, the fluid film becomes thinner, and the generated steam will flow to the other segment (i.e., the condensation segment) of the hollow cavity in the grinding head. The steam releases heat at the condensation segment to condense into fluid, so that the fluid film is thickened. The condensate returns to a heating segment along the inner wall surface under the action of a component force of a centrifugal force. By means of such continuous evaporation, steam flow, condensation and fluid reflux, the heat is transferred from the heating segment to the condensation segment. The inner taper angle a of the hollow cavity in the nanofluid phase change heat transfer grinding head plays a turbulent flow role on the nanofluid to break the formation or sufficient development of a boundary layer on one hand so as to reinforce the heat transfer, and realizes the reflux of the nanofluid base fluid on the other hand. However, the direct processing of the inner taper angle in a grinding head matrix 87 cannot be implemented easily. As shown in FIG. 13, a hole with a certain size is drilled in the grinding head matrix 87 by a drill bit, a conical cylinder 88 with a conical inner surface is processed, the bottom of the conical cylinder 88 props against a forming surface of the drill bit to form an interference fit, the top of the conical cylinder 88 is processed into a stepped shape, the bottom of a grinding head handle I 82 is also processed into the stepped shape, and the two stepped shapes are connected by a bolt II 83 and a nut II 84 and are sealed by a gasket II 93 so as to reinforce the sealing reliability. As shown in the enlarged drawing of FIG. 14, the grinding head matrix 87 and the grinding head handle I 82 are sealed by a twisting gasket 94. The twisting gasket 94 includes an external reinforcement ring 95, filler 96 and an internal reinforcement ring 97, the filler 96 mainly plays a sealing role, the external reinforcement ring 95 plays a locating role in an installation process, and the internal reinforcement ring 97 can improve the pressure resistance of the gasket. The internal reinforcement ring and the external reinforcement ring can improve the resilience of the gasket to prevent the gasket from crushing so as to prevent sealing failure. A working chamber is dually sealed by the gasket II 93 and the twisting gasket 94 to achieve "zero leakage" of the nanofluid in the grinding process. A cooling fin I 90, a cooling fin II 91 and a cooling fin III 92 can increase the cooling area and improve the heat transfer efficiency. A shaft shoulder is processed on the grinding head matrix 87 to locate the cooling fins 90, 91, 92, and a sleeve I 85 and a sleeve II 86 can prevent movement of the cooling fins. Abrasive grains I 89 are plated on the grinding head matrix 87. In a working process, the inner wall of the conical cylinder 88 is used as the evaporation segment of the phase change heat transfer grinding head, the cooling fins are used as the condensation segment, the heat generated in the bone grinding process is quickly transferred by the abrasive grains I 89 to the grinding head matrix 87, and then is transferred by the grinding head matrix 87 to the inner wall of the conical cylinder 88, namely the evaporation segment of the phase change heat transfer grinding head, the nanofluid base fluid in the evaporation segment is evaporated and vaporized, the steam flows to the condensation segment under a small pressure difference to release heat to condense into fluid, and the fluid flows back to the evaporation segment under the action of the centrifugal force to complete a working cycle. This cycle reduces the temperature in the grinding area so as to avoid secondary injury to the human body. Table 1 and table 2 list the nanofluid base fluid suitable for the device, which is fluid at room temperature and will be evaporated into gas when the grinding reaches a certain temperature, and table 3 lists the heat conductivity coefficients of commonly used nanoparticles. The mass fraction of the nanofluid is generally 2%-8%, a certain proportion of nanoparticles are added in the base fluid to form nanoparticle suspension, and then a corresponding surfactant is added with the aid of ultrasonic vibration according to the category and physicochemical properties of the base fluid to obtain stably suspending nanofluid. The configured nanofluid is placed in the hollow cavity of the phase change heat transfer grinding head, and then the effect of reducing the grinding temperature to reduce the secondary injury to the patient in the surgical process can be achieved.

TABLE 1

Boiling points of commonly used pure nanofluid base fluid

| | Material | | | | |
|---|---|---|---|---|---|
| | Carbon disulfide | Dichloro-methane | Diethyl ether | Pentane | Petroleum ether |
| Molecular formula | $CS_2$ | $CH_2Cl_2$ | $C_2H_5OC_2H_5$ | $C_5H_{12}$ | $C_7H_7BrMg$ |
| Boiling point (° C.) | 46.5 | 39.8 | 34.6 | 36.1 | 30-60 Constant boiling range |

TABLE 2

Boiling points of commonly used azeotropic mixture nanofluid base fluid

| | Material | | | | |
|---|---|---|---|---|---|
| | water-diethyl ether | Methanol-dichloromethane | Water-carbon disulfide | Methanol-benzene | Methanol-methyl formate-cyclohexane |
| Composition (w/w) | 1.0-99.0 | 7.3-92.7 | 2.0-98.0 | 39-61 | 17.8-48.6-33.6 |
| Boling point (° C.) | 34 | 37.8 | 44 | 48.3 | 50.8 |

TABLE 3

Heat conductivity coefficients of commonly used nanoparticles

| | Material | | | | | | | |
|---|---|---|---|---|---|---|---|---|
| | Copper oxide | Aluminum oxide | Silicon | Aluminum | Copper | Diamond | Carbon nanotube | Graphene |
| conductivity coefficient $W(m \cdot K)^{-1}$ | 19.6 | 40 | 148 | 237 | 401 | 2300 | 3000 | 5000 |

Figure 15A:
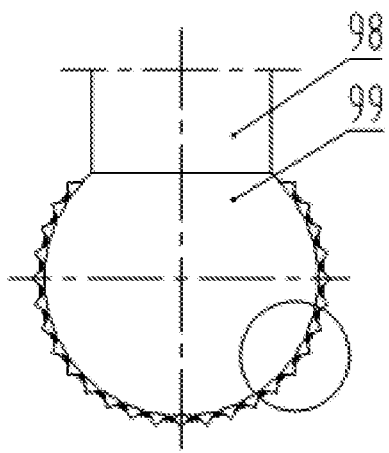
FIG. 15(a) is a structural schematic diagram of a sixth embodiment.
Figure 15B:
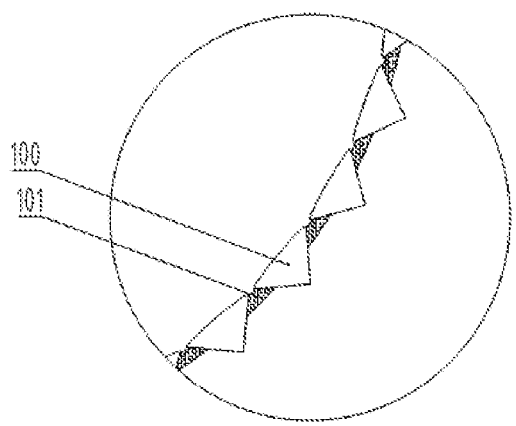
FIG. 15(b) is an enlarged drawing at a marked in FIG. 15(a)

The sixth embodiment of the present invention is a hydrophilic grinding head. As shown in FIG. 15(a) and FIG. 15(b), a grinding head handle II 98 is clamped on the electric spindle 28, abrasive grains II 100 are attached to a grinding head II 99, and micron-sized $TiO_2$ 101 is attached to the surroundings of the abrasive grains II 100. The abrasive grains II 100 and the micron-sized $TiO_2$ 101 are attached to the grinding head II 99 in an electroplating mode. Since the micron-sized $TiO_2$ 101 is hydrophilic, the cooling fluid can be easily attached to the abrasive grains in the grinding process, thus effectively enhancing the heat dissipation of the grinding area.

Figure 16:
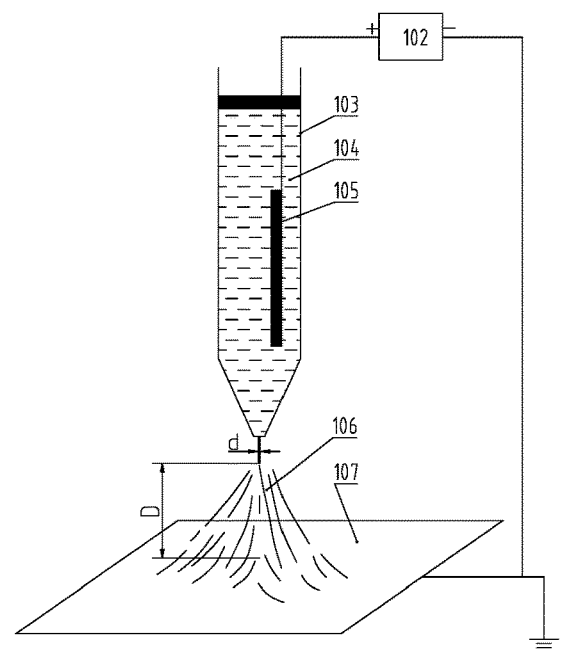
FIG. 16 is a working principle diagram of a seventh embodiment.
Figure 17:
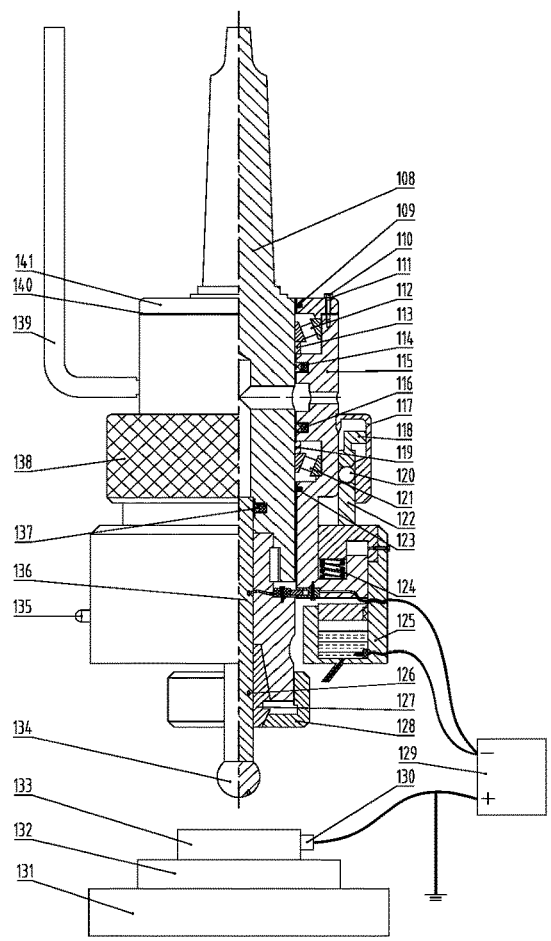
FIG. 17 is a semi-sectional view of the seventh embodiment.
Figure 18:
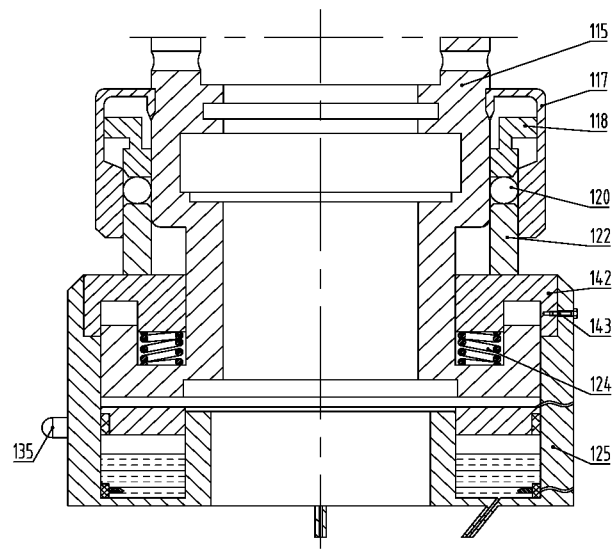
FIG. 18 is a sectional view of a telescopic sleeve structure in the seventh embodiment.
Figure 19A:
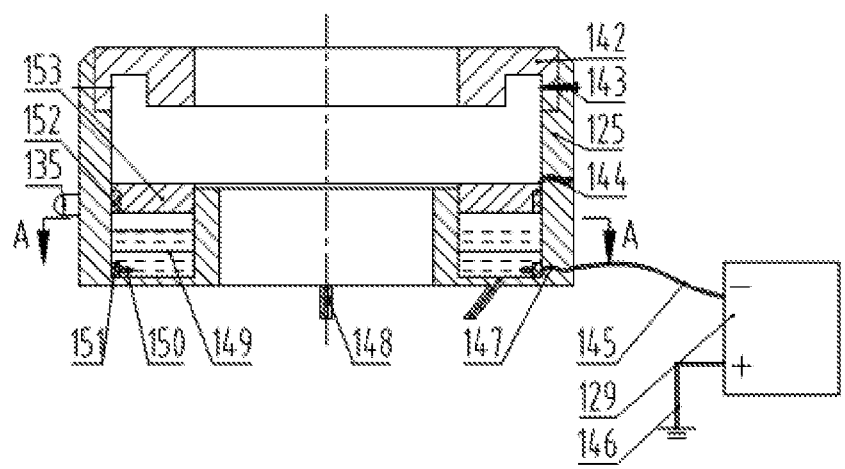
FIG. 19(a) is a sectional view of an electrostatic atomization film formation structure in the seventh embodiment.
Figure 19B:
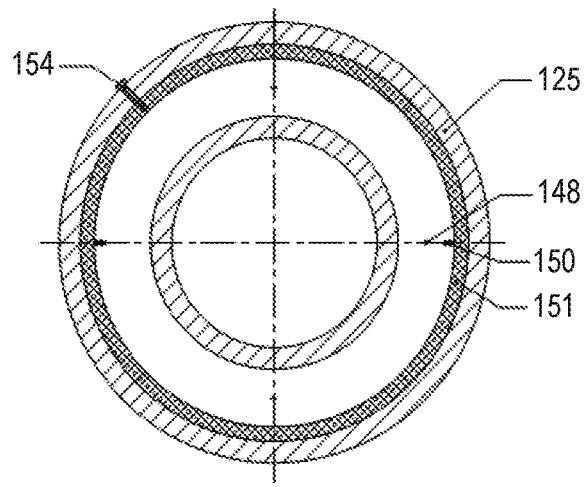
FIG. 19(b) is a sectional view of the FIG. 19(a) along the A-A direction.
Figure 20:
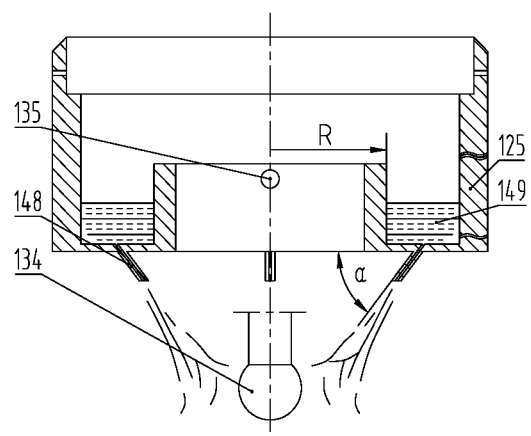
FIG. 20 is a schematic diagram of an angle of a nozzle of the electrostatic atomization film formation structure in the seventh embodiment.
Figure 21:
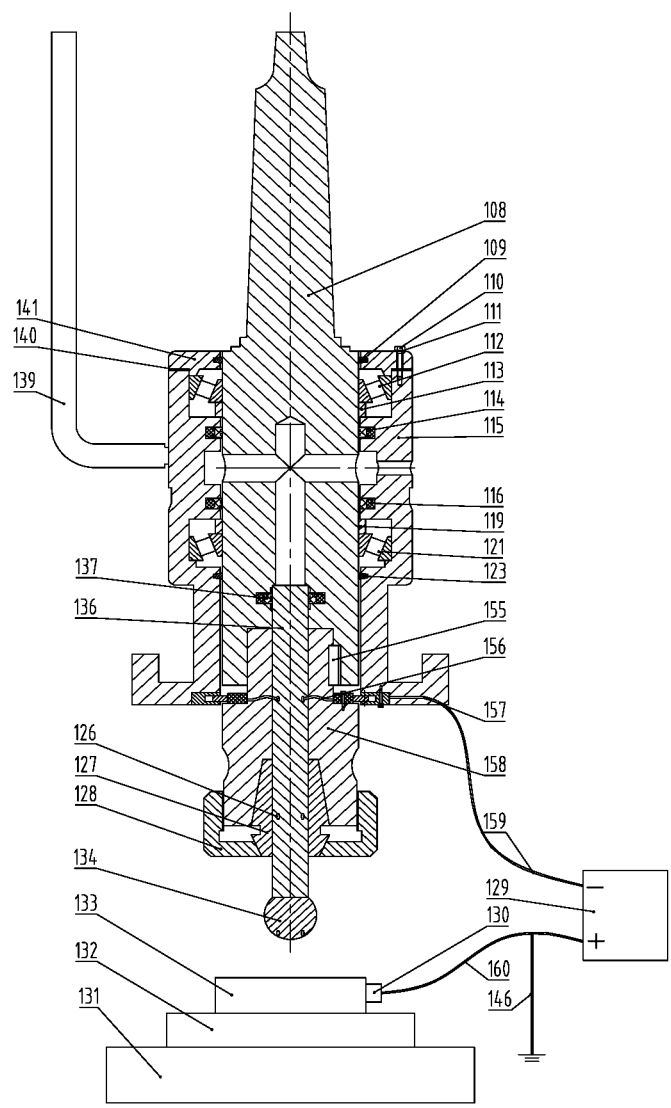
FIG. 21 is a structural sectional diagram of an electrostatic atomization internal cooling grinding structure in the seventh embodiment.
Figure 22:
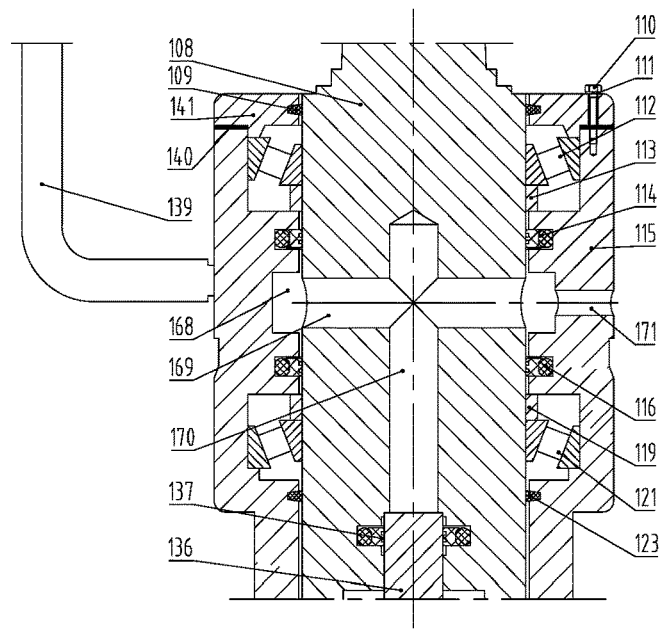
FIG. 22 is a schematic view of the sealing structure and a schematic diagram showing a flow direction of cooling fluid in the seventh embodiment.
Figure 23:
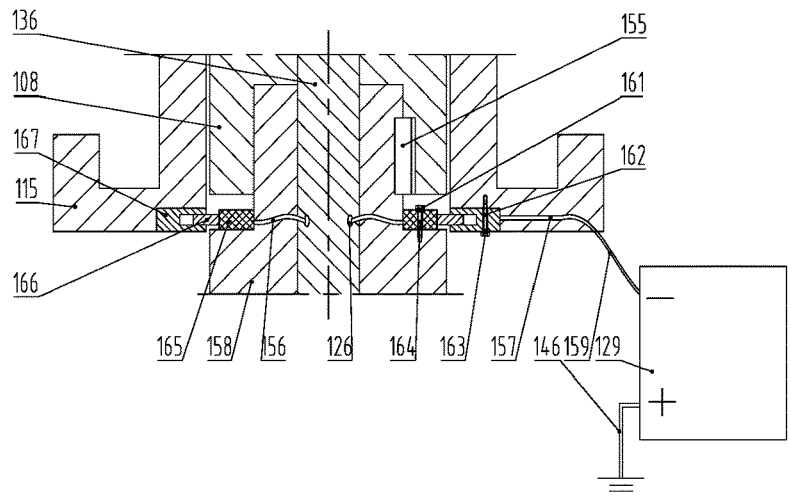
FIG. 23 is a sectional view of the electrostatic atomization structure in the seventh embodiment.

The seventh embodiment of the present invention is a telescopic sleeve type electrostatic atomization film formation internal cooling grinding device. FIG. 16 is a working principle diagram thereof, as shown in this figure, a spinning medium I 104 is a polymer solution or a melt, which is contained in the injection pump I 103 and is inserted into a metal electrode 105. The electrode is connected to a high voltage electrostatic generator 102 to charge the fluid. A grounded receiving plate 107 serves as a cathode. When the electric field is not started, the injection pump I 103 provides a continuous constant thrust for a piston, and the spinning medium I 104 in the injection pump I 103 is extruded onto a syringe needle at a fixed rate. When the high voltage electric field is not started, a spinning solution forms droplets under the synergistic effect of its own gravity, its own viscosity and the surface tension, and the droplets are suspended on the jet orifice. When the electric field is started, charges will be formed on the surface of the polymer solution, and mutual exclusiveness of the charges and the compression of opposite charge electrodes to the charges on the surface will generate a force opposite to the surface tension. When the voltage is not large enough, the surface tension on the surfaces of the droplets will prevent the droplets from being jetted out, and thus the droplets are maintained at the nozzle. When the applied voltage increases, the hemispherical surface of the droplet that is about to drop will be distorted into a cone, the increase of the applied voltage is continued, and when the voltage exceeds a certain critical value, the charged part in the solution overcomes the surface tension of the solution to form a charged jet flow so as to be jetted out from the nozzle. Under the action of the electric field, when the jet flow 106 is stretched to a certain extent, the jet flow will bend and generate a further split stretch phenomenon, the specific surface area of the jet flow 106 increases quickly at the moment to quickly volatilize the solvent, and the jet flow is finally collected on a collection net and is cured into a non-woven-shaped fibrofelt. The high voltage electrostatic generator 102 generally selects the high voltage of 5-20 kV, in addition, a positive voltage field is conducive to the release of the charges on the surfaces of the fibers, while a negative voltage field can provide a more stable electric field force, the two voltage fields generate different impacts on the electrostatic atomization film formation of different polymers.

The specific structure of the telescopic sleeve type electrostatic atomization film formation internal cooling grinding device in the embodiment is as shown in FIG. 17, and can be divided into three parts: a telescopic sleeve structure, an electrostatic atomization film formation structure and an electrostatic atomization internal cooling grinding structure. The telescopic sleeve structure is used for adjusting the distance between a jet orifice 148 and a workpiece 133, so that nanofibers are successfully cured on the workpiece 133 to form a film. The electrostatic atomization film formation structure is a device used for atomizing the spinning medium into droplets, curing the droplets into fibers and enabling the fibers to form a film at last. The internal cooling grinding structure is a main grinding part and is used for the workpiece 133 by grinding.

FIG. 18 shows a sectional view of the telescopic sleeve structure. A hand rotating sleeve 117 is fixed on a fixing jacket 115 through a groove in the fixing jacket 115, and a push plate I 118 is in threaded connection with the hand rotating sleeve 117. Antiskid stripes 138 are arranged on the outer surface of the hand rotating sleeve 117 to prevent the hand rotating sleeve 117 from skidding when the same is rotated. If the hand rotating sleeve 117 is rotated clockwise, the push plate I 118 will move downward through the threaded connection to push a ball 120 to roll downward, and then the roller pushes a push plate II 122 and the push plate connecting block 142 to move downward in sequence. The push plate connecting block 142 is connected with an injection pump II 125 by a screw X 143, thereby pushing the injection pump II 125 to move downward. Since the fixing jacket 115 is fixed in the up and down direction, when the push plate connecting block 142 moves downward, a spring 124 will be compressed. A plurality of springs 124 are provided, and the lower ends of the springs are fixed on the fixing jacket 115. If the hand rotating sleeve 117 is rotated counterclockwise, the pressure applied to the spring 124 is reduced, the spring 124 extends out and sequentially pushes the push plate connecting block 142, the push plate II 122 and the ball 120 to move or roll upward. Therefore the extension and retraction of the sleeve structure are realized.

As shown in FIG. 19(*a*) and FIG. 19(*b*), a pressure cavity composed of the injection pump II 125 and a plunger 153 is filled with a spinning medium II 149. The plunger 153 is connected with the motor through a conducting wire placement groove I 144, and a sealing ring III 152 is arranged on an outer circle of the plunger 153. An electrode disc 151 is arranged at a bottom end of the injection pump II 125, and the electrode disc 151 is fixed on the injection pump II 125 by four screws XI 154. The electrode disc 151 has two electrodes 150, and is connected with an adjustable high voltage DC power supply 129 through a conducting wire placement groove II 147 to charge the fluid. The motor 150 is connected with the negative electrode of the adjustable high voltage DC power supply 129 through the electrode disc 151 and a conducting wire I 145, the positive electrode of the adjustable high voltage DC power supply 129 is connected with a workpiece powering device 130 and is grounded by a grounding wire 146. An electrostatic spinning structure is adjusted to a proper height, after the control system gives a movement instruction, the plunger 153 moves downward to provide a continuous and constant thrust for a pressure cavity, the spinning medium II 149 is extruded onto the jet orifice 148 at a fixed rate, and the spinning medium forms droplets under the synergistic effect of the gravity, the viscosity and the surface tension thereof, and the droplets are suspended on the jet orifice. The external voltage is adjusted to a proper voltage, so that the spinning medium II 149 is jetted out from the jet orifice 148 in the form of jet flow. When the jet flow is stretched to a certain extent, the jet flow will bend and generate a further split stretch phenomenon, and as the specific surface area of the jet flow increases quickly at the moment, the solvent is quickly volatilized, and finally is collected on a collection net and cured into a non-woven-shaped fibrofelt. The device can be provided with one or more jet orifices, and three jet orifices are provided in the present invention. In the actual operation, an indicator lamp 135 faces to a grinding feed direction, namely fibers jetted out from the jet orifice drop onto a ground wound.

As shown in FIG. 20, the jet orifice 148 has an inclination angle α, which can be obtained by drilling an oblique hole in the bottom surface of the injection pump II 125. In the design, the R value of the inner wall of the injection pump II 125 can also be properly decreased, and the jet orifice 148 is designed to a vertical structure.

FIG. 21 shows a sectional structure of the electrostatic atomization internal cooling grinding structure. As shown in this figure, a locating shaft 139 is fixed to a machine tool, and since the locating shaft 139 is integrated with the fixing jacket 115, the fixing jacket 115 is also static. The Mohs spindle 108 is connected to a machine tool spindle and rotates with the machine tool spindle. As shown in FIG. 22, two holes penetrating through each other are formed in the Mohs spindle 108, a horizontal hole 169 is a through hole, and a pressure cavity 168 is located on one side of the horizontal hole 169. A cooling fluid inlet 171 is formed in the fixing jacket 115, and the cooling fluid sequentially enters an annular groove in the fixing jacket 115 and the horizontal hole 169 of the Mobs spindle 108 from the hole, flows into a vertical hole 170 and enters an internal cooling hole of an internal cooling grinding head handle 136 under the pressure of an external pump. Since the cooling fluid is subjected to a certain pressure in the annular groove in the fixing jacket 115 and in the annular groove in the Mohs spindle 108 at the upper end of the grinding head handle 136, the device adopts a rotary sealing ring I 114, a rotary sealing ring II 116 and a rotary sealing ring III 137 as sealing devices. In the actual operation, the grinding device forms a certain angle with the horizontal plane, the internal cooling grinding head handle 136 needs to bear forces in two directions: the axial direction and the radial direction, then the Mohs spindle 108 also needs to bear the forces in two directions: the axial direction and the radial direction, therefore the device adopts a tapered roller bearing I 112 and a tapered roller bearing II 121. The tapered roller bearing I 112 is located by an end cover 141 and a sleeve III 113, and the tapered roller bearing II 121 is located by the fixing jacket 115 and a sleeve IV 119. Both ends of the bearings are sealed by a sealing ring I 109 and a sealing ring II 123 to prevent leakage of lubricating oil. The end cover 141 is fixed on the fixing jacket 115 by a screw IX 110 and a gasket III 111, and a gasket IV 140 can adjust the gaps and backlashes of the bearings and the axial position of the spindle. In an installation process, the internal cooling grinding head handle 136 is installed in the hole in the lower end of the Mohs spindle 108 at first, then a chuck 127 is installed, and finally, a locking nut 128 is screwed down by the Mohs spindle 108 and the threads of the locking nut 128.

FIG. 23 is a sectional view of the electrostatic atomization structure. A conducting wire connecting block 165 is fixed on a grinding head handle clamping body 158 by a gasket V

161 and a screw XIII 164. Two conducting wires II 156 of the conducting wire connecting block 165 stretch into an internal cooling hole 126 of the internal cooling grinding head handle 136. The Mohs spindle 108 rotates and drives the grinding head handle clamping body 158 to rotate by a flat key 155, and a high voltage conversion device 167 is fixed on the fixing jacket 115 by a gasket VI 163 and a screw XII 162 and is static. A roller 166 is integrated with the conducting wire connecting block 165 and rotates in the inner groove of the high voltage conversion device 167, so that high voltage is transferred from a fixed high-voltage outer conducting wire III 159 to a rotary high-voltage inner conducting wire II 156. Due to a low corona inception voltage of negative corona discharge during corona discharge and a high breakdown voltage, the high voltage conversion device 167 can be connected with the negative electrode of the adjustable high-voltage DC power supply 129 through a conducting wire placement groove III 157 and a conducting wire III 159 so as to charge the fluid, and the positive electrode of the adjustable high-voltage DC power supply 129 is connected with the workpiece powering device 130 through a conducting wire IV 160 and is grounded by the grounding wire 146. The workpiece 133 is installed on a force measurement instrument II 132, and the force measurement instrument II 132 is magnetically adsorbed on a working table II 131. The charge principle of the droplets of the electrostatic atomization device is as follows: when the negative electrode of the power supply discharges, a large number of ions will be generated in a corona area, positive ions will move to the cathode of the electrode and generate electrical neutralization, and negative ions and electrons will move towards the anode to enter a drift area and collide with the droplets in the drift area to be attached to the droplets, so that the droplets become charge carriers and carry charges having the same polarity as the electrode. After the droplets jetted out from the nozzle are charged, the droplets move in a fixed direction under the action of the electric field force to cover the surface of the workpiece maximally. In the charge process, the surface of the nanoparticles is relatively large, the surface polarity is strong, after being charged, the nanoparticles have a larger charge-mass ratio than the droplets, so the nanoparticles tend to reach the workpiece earlier, and then the ideal heat transfer capacity thereof can be better used. An "electrostatic encircling" effect exists in the electrostatic field, therefore when the droplets and the nanoparticles move toward the workpiece, they can enter a depression on a surface having certain roughness of the workpiece, therefore the relative coverage area is expanded, and better lubrication and heat transfer effects can be achieved.

Figure 24:
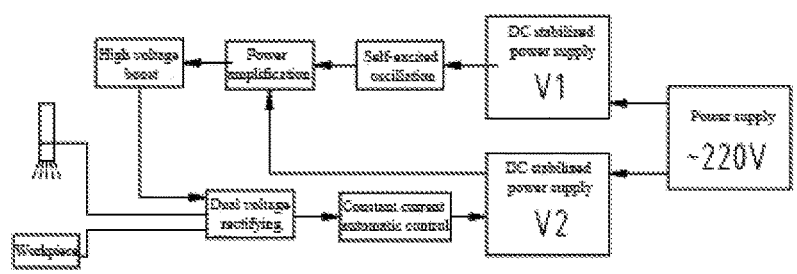
FIG. 24 shows electrostatic atomization and a block diagram of a circuit system of the electrostatic atomization film formation structure in the seventh embodiment.

As shown in FIG. 24, the adjustable high voltage DC power supply 129 is composed of an AC power input unit, a DC voltage regulating unit V1, a DC voltage regulating unit V2, a self-excited oscillating circuit, a power amplifier circuit, a high frequency pulse booster, a voltage doubling rectifying circuit and a constant current automatic control circuit.

Figure 25A:
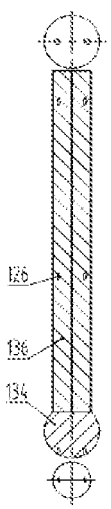
FIG. 25(a) is a schematic diagram of an internal cooling hole of an internal cooling grinding structure in the seventh embodiment.
Figure 25B:
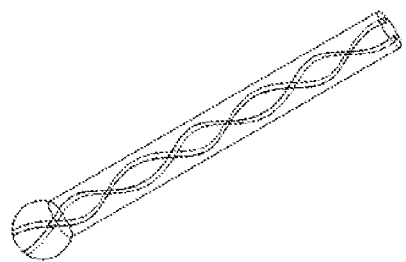
FIG. 25(b) is a schematic diagram of an internal structure of the internal cooling grinding structure in the seventh embodiment.

As shown in FIG. 25(*a*) and FIG. 25(*b*), the internal cooling hole 126 is a double-helical pore and penetrates through the bottom end of the internal cooling grinding head 134 from the top end of the internal cooling grinding head handle 136. Compressed air, the cooling fluid or the nano-fluid is directly sprayed to the grinding area after being accelerated in two helical holes in the grinding process, so that the temperature in the grinding area can be effectively reduced, and the abrasive dust is brushed away, thus the service life of the cutter is prolonged.

The specific working process of the present invention is as follows:

The present invention involves 7 embodiments, all of which disclose a high-speed grinding surgery experimental platform. The experimental device is mainly composed of the linear three-axis platform, the electric spindle 28, the force measurement instruction I 22, the thermocouple 10 and the control system 4. The linear three-axis platform can achieve movement in X, Y and Z directions, the electric spindle 28 clamps the grinding tool and drives the grinding tool to rotate at a high speed, the force measurement instruction I 22 measures the grinding force in the grinding process, the thermocouple 10 measures the temperature, and the control system 4 controls the movement of the linear three-axis platform and the electric spindle 28, and analyzes the grinding force and grinding temperature signals.

The first embodiment and the second embodiment are respectively drip cooling and flood cooling, and the fluid paths are separately composed of the fluid storage tank I 57, the hydraulic pump I 56, the pressure regulating valve I 55 and the throttle valve I 54, which are connected in sequence. The fluid storage tank I 57 is filled with the normal saline, the normal saline in the fluid storage tank I 57 is pumped out by the hydraulic pump I 56 and enters the nozzle through the pressure regulating valve I 55 and the throttle valve I 54. The overflow valve I 58 and the recycling bin I 59 form the protection path. The normal saline is used as the cooling fluid, as the flow velocity of the cooling fluid in the drip cooling mode is very low, and the flow velocity of the cooling fluid in the flood cooling mode is relatively high, the hydraulic pump I 56 is the variable frequency water pump, and the flow thereof can be controlled by regulating the pressure to obtain the ideal flow velocity.

The third embodiment and the fourth embodiment are the MQC and the Nano-MQC, the normal saline and the nano-fluid are separately used as coolants, the pneumatic atomizing nozzles are adopted in both the MQC and the Nano-MQC, and the MQC and the Nano-MQC separately involve the fluid path and the gas path. The fluid path is composed of the fluid storage tank II 71, the hydraulic pump II 70, the pressure regulating valve III 69, the throttle valve II 61 and the turbine flowmeter I 60, which are connected in sequence, and the gas path is composed of the air compressor 68, the filter 67, the gas storage tank 65, the pressure regulating valve II 64, the throttle valve III 63 and the turbine flowmeter II 62, which are connected in sequence. During working, hydraulic pump II 70 is started, the coolant stored in the fluid storage tank II 71 enters the fluid injection channel joint 74 of the nozzle through the fluid pressure regulating valve III 69, the fluid throttle valve II 61 and the turbine flowmeter I 60. The overflow valve II 72 acts as the safety valve, and the overflow valve II 72 is opened when the pressure in the fluid path exceeds the set pressure, so that the coolant returns into the recycling bin II 73 through the overflow valve II 72. While the overflow valve II 72 is started, the air compressor 68 is started, high pressure gas enters the gas injection channel joint 75 of the nozzle through the filter 67, the gas storage tank 65, the gas pressure regulating valve II 64, the gas throttle valve III 63 and the turbine flowmeter II 62, and the pressure gauge 66 monitors the pressure value in the gas path. The high pressure gas enters the mixing chamber 81 through gas holes 76 distributed in the gas hole wall 80, is fully mixed and atomized with the normal saline from the fluid injection channel joint 74 in the nozzle mixing chamber 81 and enters the swirl chamber 78 after being accelerated in the acceleration chamber 79, so that the high pressure gas and the normal saline are further mixed and accelerated and are jetted to the grinding area from the nozzle outlet in the form of atomized droplets. The optimal minimum quantity cooling effect can be achieved by regulating the pressure regulating valves, the throttle valves and the flowmeters in the gas path and the fluid path, and by regulating the pressure and the flow of the high pressure gas. The nanofluid can be prepared from the normal saline and hydroxyapatite.

The fifth embodiment is the nanofluid phase change heat transfer grinding head. The hole with a certain size is drilled in the grinding head matrix 87 by the drill bit, the conical cylinder 88 with the conical inner surface is processed by lathing, the bottom of the conical cylinder 88 props against the forming surface of the drill bit to form an interference fit, the top of the conical cylinder 88 is processed into the stepped shape, the bottom of the grinding head handle I 82 is also processed into the stepped shape, and the two stepped shapes are connected by the bolt II 83 and the nut II 84 and are sealed by the gasket II 93 so as to reinforce the sealing reliability. The grinding head matrix 87 and the grinding head handle I 82 are sealed by the twisting gasket 94. The twisting gasket 94 includes the external reinforcement ring 95, the filler 96 and the internal reinforcement ring 97, the filler 96 mainly plays the sealing role, the external reinforcement ring 95 plays the locating role in the installation process, and the internal reinforcement ring 97 can improve the pressure resistance of the gasket. The internal reinforcement ring and the external reinforcement ring can improve the resilience of the gasket to prevent the gasket from crushing so as to prevent sealing failure. The working chamber is dually sealed by the gasket II 93 and the twisting gasket 94 to achieve "zero leakage" of the nanofluid in the grinding process. The cooling fin I 90, the cooling fin II 91 and the cooling fin III 92 can increase the cooling area and improve the heat transfer efficiency. The shaft shoulder is processed on the grinding head matrix 87 to locate the cooling fins 90, 91, 92, and the sleeve I 85 and the sleeve II 86 can prevent movement of the cooling fins. The abrasive grains I 89 are plated on the grinding head matrix 87. In the working process, the inner wall of the conical cylinder 88 is used as the evaporation segment of the phase change heat transfer grinding head, the cooling fins are used as the condensation segment, the heat generated in the bone grinding process is quickly transferred by the abrasive grains I 89 to the grinding head matrix 87, and then is transferred by the grinding head matrix 87 to the inner wall of the conical cylinder 88, namely the evaporation segment of the phase change heat transfer grinding head, the nanofluid base fluid in the evaporation segment is evaporated and vaporized, the steam flows to the condensation segment under a small pressure difference to release heat to condense into fluid, and the fluid flows back to the evaporation segment under the action of the centrifugal force to complete a working cycle. This cycle reduces the temperature in the grinding area so as to avoid secondary injury to the human body.

The sixth embodiment is the hydrophilic grinding head. The grinding head handle II 98 is clamped on the electric spindle 28, the abrasive grains II 100 are attached to the grinding head II 99, and the micron-sized $TiO_2$ 101 is attached to the surroundings of the abrasive grains II 100. Since the micron-sized $TiO_2$ 101 is hydrophilic, the cooling fluid can be easily attached to the abrasive grains in the grinding process, thus effectively enhancing the heat dissipation of the grinding area.

The seventh embodiment is an integrated device of an electrostatic atomization internal cooling grinding tool and an electrostatic atomization film formation structure, which can be divided into three parts: the telescopic sleeve structure, the electrostatic atomization film formation structure and the electrostatic atomization internal cooling grinding structure. The telescopic sleeve structure is used for adjusting the distance between the jet orifice 148 and the workpiece 133, so that nanofibers are successfully cured on the workpiece 133 to form the film. The electrostatic atomization film formation structure is a device used for atomizing the spinning medium into droplets, curing the droplets into fibers and enabling the fibers into the film at least. The internal cooling grinding structure is the main grinding part and is used for removing the workpiece 133 by grinding.

The antiskid stripes 138 are arranged on the outer surface of the hand rotating sleeve 117 to prevent the hand rotating sleeve 117 from skidding when the same is rotated. If the hand rotating sleeve 117 is rotated clockwise, the push plate I 118 will move downward through the threaded connection to push the ball 120 to roll downward, and then the ball pushes the push plate II 122 and the push plate connecting block 142 to move downward in sequence. The push plate connecting block 142 is connected with the injection pump II 125 by the screw X 143, thereby pushing the injection pump II 125 to move downward. Since the fixing jacket 115 is fixed in the up and down direction, when the push plate connecting block 142 moves downward, the spring 124 will be compressed. A plurality of springs 124 are provided, and the lower ends of the springs are fixed on the fixing jacket 115. If the hand rotating sleeve 117 is rotated counterclockwise, the pressure applied to the spring 124 is reduced, the spring 124 extends out and sequentially pushes the push plate connecting block 142, the push plate II 122 and the ball 120 to move or roll upward. Therefore the extension and retraction of the sleeve structure are realized.

The electrostatic spinning structure is adjusted to the proper height, after the control system gives the movement instruction, the plunger 153 moves downward to provide the continuous and constant thrust for the pressure cavity, the spinning medium II 149 is extruded onto the jet orifice 148 at the fixed rate, and the spinning medium forms the droplets under the synergistic effect of the gravity, the viscosity and the surface tension thereof, and the droplets are suspended on the jet orifice. The external voltage is adjusted to the proper voltage, so that the spinning medium II 149 is jetted out from the jet orifice 148 in the form of jet flow. When the jet flow is stretched to a certain extent, the jet flow will bend and generate the further split stretch phenomenon, and as the specific surface area of the jet flow increases quickly at the moment, the solvent is quickly volatilized, and finally is collected on the collection net and cured into the non-woven-shaped fibrofelt. The locating shaft 139 is fixed to the machine tool, and since the locating shaft 139 is integrated with the fixing jacket 115, the fixing jacket 115 is also static. The Mohs spindle 108 is connected to the machine tool spindle and rotates with the machine tool spindle. The cooling fluid sequentially enters the annular groove in the fixing jacket 115 and the horizontal hole of the Mobs spindle 108 from the hole, flows into the vertical hole and enters the internal cooling hole of an internal cooling grinding head handle 136 under the pressure of an external pump. In the installation process, the internal cooling grinding head handle 136 is installed in the hole in the lower end of the Mohs spindle 108 at first, then the chuck 127 is installed, and finally, the locking nut 128 is screwed down by the Mohs spindle 108 and the threads of the locking nut 128.

Two conducting wires II 156 of the conducting wire connecting block 165 stretch into the internal cooling hole 126 of the internal cooling grinding head handle 136. The Mohs spindle 108 rotates and drives the grinding head handle clamping body 158 to rotate by the flat key 155, and the high voltage conversion device 167 is fixed on the fixing jacket 115 by the gasket VI 163 and the screw XII 162 and is static. The roller 166 is integrated with the conducting wire connecting block 165 and rotates in the inner groove of the high voltage conversion device 167, so that high voltage is transferred from the fixed high-voltage outer conducting wire III 159 to the rotary high-voltage inner conducting wire II 156. The high voltage conversion device 167 is connected with the negative electrode of the adjustable high-voltage DC power supply 129 through the conducting wire placement groove III 157 and the conducting wire III 159 so as to charge the fluid, and the positive electrode of the adjustable high-voltage DC power supply 129 is connected with the workpiece powering device 130 and is grounded by the grounding wire 146.

As shown in Table 4, the electrostatic spinning system applied to wound dressings mainly includes natural macromolecules and synthetic polymers. By adoption of the electrostatic spinning technology, these materials show auxiliary healing ability on promotion of the formation of epithelium in wound healing experiments in vivo and in vitro.

means of the high-speed stretching of the electric filed force within a shorter distance, and solvent evaporation and curing to form polymer fibers. This process is electrostatic spinning. When the charged droplet is introduced into the electric field, charges accumulate on the surface of the droplet, resulting in a charge repulsion (expressed as an electrostatic pressure on the surface of the charged droplet $P_E = \sigma^2/2\varepsilon_0$, and related to charge density $\sigma$ on the surface of the droplet and a vacuum dielectric constant $\varepsilon_0$), which drives the droplet to split out and forms an unsteady balance with the surface tension (expressed as a pressure $P_C = 2\gamma/R$ related to the surface tension $\gamma$ of the fluid on the tail end of the nozzle and the radius R of the droplet) tending to shrink the droplet on the surface of the droplet, and the balance can be used expressed by the following formula:

$$\Delta P = 2\gamma/R - e^2/(32\varepsilon_0 \pi^2 R^4) \qquad (1)$$

In the formula, e represents the total charges of the droplet; and R represents the radius of the droplet.

It can be seen that the pressure generated by static electricity increases as the radius of the droplet decreases (the charge density increases). When the tension generated on the surface of the droplet is equal to the electrostatic

TABLE 4

Polymer solution system capable of carrying out electrostatic spinning

| Natural polymer | Solvent system | Synthetic polymer | Solvent system |
|---|---|---|---|
| Collagen | Hexafluoroisopropanol | Polylactic acid | Mixed solvents of tetrahydrofuran, dichloromethane, chloroform, acetone and the like with N,N-dimethylformamide, N,N-dimethylacetamide and the like |
| Collagen/PEO | Acetic acid, water/sodium chloride | Polyglycolic acid | |
| Collagen/polycaprolactone | Dichlormethane(trichloromethane)/hexafluoroisopropanol | Polycaprolactone | |
| Gelatin/polycaprolactone | 2,2,2-trifluoroethanol | Polybutyl ester | |
| Gelatin | 2,2,2-trifluoroethanol, hexafluoroisopropanol | Polystyrene | |
| Gelatin/PEO | Water/sodium chloride | Polystyrene | |
| Silk fibroin | Hexafluoroisopropionic acid | Polycarbonate | |
| Fibroin/PEO | Water | Polyamide | |
| Fibrous protein | Hexafluoroisopropanol | Polyethylene glycol terephthalate | |
| Chitin | Hexafluoroisopropanol | Polyurethane | |
| Chitosan | Formic acid, trifluoroacetic acid | Polyvinyl chloride | |
| Cellulose | Acetic acid | Polymethyl methacrylate | |
| Casein/PVA | NMO/water | Polyvinylidene fluoride | |
| BSA/PVA | Water | | |
| Luciferase/PVA | Water | | |

Basic Theory of Electrostatic Spinning:

When the applied voltage exceeds the critical value, micromolecular charged fluid or macromolecular charged fluid with low viscosity will be jetted out from the nozzle to form tinny charged droplets, and move in a direction opposite to the electrode to form dispersed micro-nano-sized aerosol or polymer heads, and this process is electrostatic atomization. If the charged fluid is a polymer solution or a melt, its molecular chains entangle together, in the process of applying high voltage static electricity to the fluid, when the charge repulsion on the fluid surface exceeds its surface tension, polymer jet flows will be jetted out from a Tyler cone surface at the tail end of the nozzle at a high speed, these jet flows are finally deposited on the receiving plate by repulsion, the charged droplet in the electric field reaches equilibrium, assuming that the diameter of the charged droplet is D at this time and is converted into the charge density on the surface of the droplet to obtain the following formula:

$$e/M = \sqrt{[(288\varepsilon_0\gamma)/(\rho^2 D^3)]} \qquad (2)$$

In the formula, M represents the mass of the droplet.

When the charge repulsion exceeds this limit, the droplet at the tail end of the nozzle will be split into a plurality of small droplets to form the electrostatic atomization phenomenon. The stable limit of the droplet is called the "Rayleigh stability limit". Assuming that the fluid jet flow is cylindrical, and then the condition of the "Rayleigh stability limit" can be expressed as follows:

$$\Delta P = \gamma/R - \tau^2/(8\varepsilon_0 \pi^2 R^4) \qquad (3)$$

In the formula, τ represents the charges carried in a length unit of the fluid jet flow and is converted into the charge density on the surface of the jet flow as follows:

$$e/M = \sqrt{[(64\varepsilon_0 \gamma)/(\rho^2 D^3)]} \qquad (4)$$

It can be seen from the above formula that when the condition of the "Rayleigh stability limit" is satisfied, the charges required for forming the cylindrical jet flow on the Taylor cone surface are less than those required for electrostatic atomization, and this particular case is electrostatic spinning.

The computational formula of a critical voltage of the jet flow jetted out from the top end of the Taylor cone is:

$$V^2c = (4H^2/L^2) \ast [\ln(2L/R) - 1.5] \ast (0.117\pi\gamma R_0) \qquad (5)$$

In the formula, H represents the distance between two electrodes; L represents the distance of the nozzle stretching out from a polar plate; R presents the radius of the droplet; γ represents the surface tension of the droplet; and $R_0$ represents the radius of the nozzle. (Unit: Vc is kV, H, L and R are cm, and γ is dyn/cm).

The force applied to the surface of the suspended droplet mainly includes an electric field force, viscous stress, a fluid hydrostatic pressure difference and a pressure difference caused by the surface tension. When the tangential electric field force applied to the surface of the suspended droplet is larger than the tangential viscous stress, a single jet flow or multiple jet flows are formed; and on the contrary, the droplets are formed.

The basic process of electrostatic spinning can be divided into the following three steps:

(1) The jet flow is generated and extends along a straight line. With the electrostatic spinning of a vertical downward solution as an example, polymer solution suspended microdroplets are maintained at a spinneret under the action of surface tension. When the potential difference between the jet orifice and a grounded collector increases, the movement of ions in the fluid causes the surface of the solution to be charged. These charges produce aggregation forces on the surfaces of the droplets to overcome the surface tension of the solution. As the gradual increase of the voltage, the jet flow protrudes from a cone formed by the surfaces of the suspended microdroplets to further improve the voltage, the charge density of the jet flow and the flow velocity of the jet flow are increased accordingly, and the droplets overcome the surface tension to form the jet flow.

(2) Bending instability growth and stretching thinning process of the jet flow: after the jet flow is generated, the jet flow grows along the straight line within a certain initial segment of distance. Due to the combined action of the electrostatic force and the gravity, the jet flow generates whipping at the lower end of the straight line soon. This whipping allows the jet flow to generate stretch to a very large extent in a smaller space, and then the jet flow further develops into self-similar annular flow. Each cycle is divided into three steps and the current annular flow has a smaller size than the next annular flow. First step, a smooth linear segment or a slightly bent segment develops into bent arrangement (the whipping); second step, when the bent segment of each jet flow is stretched, the linear arrangement of the bend becomes a series of circumferentially increasing spiral annular flows; and third step, when each spiral annular flow increases, the increase of the diameter of a cross section forming the annular flow is smaller, and the condition of the first step can be established along the annular flows. With the development and growth of the bending instability, the jet flow is constantly thinned, and the stretch ratio can be up to tens of thousands of times.

(3) The jet flow is cured to form nanofibers. The electric field force acting on the charged jet flow guides the entire jet flow to fly to the grounded collector, with the evaporation of the solvent or the condensation of the melt, the jet flow is cured into the nanofibers, and the nanofibers are stacked on the collector layer by layer in a spiral form, and a film-shaped or cotton fiber-shaped material is formed at last.

As shown in FIG. 16, the distance between the syringe needle and the receiving plate 107 is increased, the flying distances of the nanofibers in the air will be extended, and the diameters of the fibers decrease with the increase of the distances. A too short distance is not conducive to the full evaporation of the solvent, and a too large distance is not conducive to the collection of the nanofibers, therefore the collection distance D is generally set as 5-20 cm. When other parameters are invariable, the electrostatic voltage is increased, the field intensity of the electrostatic field is increased, and the electrostatic tensile force to the jet flow is increased, so that the diameters of the fibers decrease with the thinning of the jet flow. However, when the increase of the voltage exceeds a certain degree, the instability of the jet flow becomes more obvious, the distribution of the diameters of the fibers is widened, that is, nanofibers with large thickness differences are obtained. When the high voltage is close to 30 kV, a high-voltage end is liable to discharge to the air no matter in a dry or humid environment, the charge loss is large, the electrostatic spinning process becomes more dangerous, and thus the high voltage of 5-20 kV is generally employed under normal circumstances. In addition, a positive voltage field is favorable for the release of charges on the surfaces of the fibers, while a negative voltage field can provide a more stable electric field force, and both of which have different effects on electrostatic spinning of different polymers. The injection pump is used for conveying spinning fluid and controlling the flow velocity of the spinning fluid, and the flow velocity of the spinning fluid in a single nozzle is 0.1-10 mL/h. The syringe needle is an output port for the spinning fluid, and has an inside diameter d generally 0.1-2 mm.

The computational formula of the flow velocity is:

$$u = Q/A \qquad (6)$$

In the formula, Q represents the flow of the injection pump, and the rotating speed can be changed by regulating the frequency of inputting to a motor power supply so as to change the flow rate; and A represents the cross sectional area of the jet orifice. When n jet orifices are formed, the computational formula of A is: $A = n \cdot \pi (d/2)^2$.

Although the embodiments of the present invention have been described above in combination with the accompany drawings, the protection scope of the present invention is not limited thereto. Those skilled in the art to which the present invention pertains should be aware that, various modifications or variations obtained by those skilled in the art based on the technical solutions of the present invention without any creative effort, still fall into the protection scope of the present invention.

The invention claimed is:

1. A bone surgery grinding experimental device for cooling and electrostatic atomization film formation, the grinding experimental device comprising:

a linear three-axis platform configured to move in front and back, left and right, and up and down directions, the linear three-axis platform including an X axis structure configured to perform the left and right movement, a Y axis structure configured to perform the front and back movement, and a Z axis structure configured to perform the up and down movement;

an electric spindle;

a workpiece fixing device fixed on the Y axis structure, the electric spindle being fixed on the Z axis structure and installed at an upper end of the workpiece fixing device; and an electrostatic atomization internal cooling grinding head installed at a lower end of the electric spindle, the electrostatic atomization internal cooling grinding head including a grinding cooling device arranged in a grinding head handle or in the grinding head, the grinding cooling device including:

a Mohs spindle connecting the electrostatic atomization internal cooling grinding head to the electric spindle; and an electrostatic atomization film formation device arranged to surround the grinding head, the electrostatic atomization film formation device including a jet orifice arranged to face the electrostatic atomization internal cooling grinding head, and an electrostatic atomization film formation structure, the electrostatic atomization film formation device sleeves on an outer side of the electrostatic atomization internal cooling grinding head.

2. The grinding experimental device of claim 1, wherein:

the X axis structure is installed on a base, the X axis structure including an X axis motor, an X axis speed reducer, an X axis lead screw, and an X axis guide rod, the X axis lead screw being connected to the X axis motor through the X axis speed reducer, and the X axis guide rod is arranged to be parallel to the X axis lead screw;

the Y axis structure includes a Y axis motor, a Y axis speed reducer, a Y axis lead screw, and a Y axis guide rod, the Y axis lead screw being arranged to be perpendicular to the X axis lead screw and connected to the Y axis motor through the X axis speed reducer, and the Y axis guide rod is arranged to be parallel to the Y axis lead screw; and the Z axis structure is installed on the Y axis lead screw, the Z axis structure including a Z axis motor, a Z axis speed reducer, a Z axis lead screw, and a Z axis guide rod, the Z axis lead screw being connected with the Z axis motor through the Z axis speed reducer, the Z axis guide rod being arranged to be parallel to the Z axis lead screw, and the electric spindle is installed on the Z axis lead screw.

3. The grinding experimental device of claim 1, further comprising a workpiece grinding temperature monitoring system including a thermocouple and a thermocouple data collector, which are connected to each another, the thermocouple penetrating through a workpiece from bottom to top, the thermocouple being flush with an upper surface of the workpiece, the thermocouple data collector being connected with a control system, and the control system is connected with the grinding cooling device.

4. The grinding experimental device of claim 1, further comprising a force measurement system including a force measurement device and a force measurement instrument data collector, which are connected to each another, the force measurement instrument data collector being connected with a control system, the force measurement device including a workpiece fixing device and two force measurement instruments that are respectively installed at both ends of the workpiece fixing device, and the force measurement instruments are connected with the force measurement instrument data collector.

5. The grinding experimental device of claim 1, wherein the grinding cooling device is one of a drip cooling device, a flood cooling device, a Nano-MQC device, a phase change heat transfer cooling device, or an electrostatic atomization internal cooling device.

6. The grinding experimental device of claim 1, wherein:

the electrostatic atomization internal cooling grinding structure includes a grinding head, a conducting wire connecting block, a high voltage conversion device, and a power supply, a grinding head handle of the grinding head is fixed in the Mohs spindle, the conducting wire connecting block is fixed to the Mohs spindle, the high voltage conversion device is installed on the fixing jacket, the conducting wire connecting block is movably connected with the high voltage conversion device, the high voltage conversion device is connected with the power supply, an internal cooling hole is formed in the grinding head handle, the internal cooling hole penetrating through the grinding head and the grinding head handle, the conducting wire connecting block is connected with the internal cooling hole through a conducting wire, and the internal cooling hole is a double-helical pore passage.

7. The grinding experimental device of claim 1, wherein:

the electrostatic atomization film formation structure includes an injection pump, an electrode disc installed to fit an inner wall of the injection pump, an electrode component fixed on the electrode disc, and the jet orifice formed in an outlet end of the injection pump, the electrode component and a workpiece powering device are respectively connected with a negative electrode and a positive electrode of an electrostatic generator, a plunger of the injection pump is connected with a motor, and the jet orifice is vertically formed and is formed to incline toward the grinding head.

8. The grinding experimental device of claim 1, wherein:

the electrostatic atomization internal cooling grinding head includes a telescopic sleeve structure, the telescopic sleeve structure including a hand rotating sleeve and a push plate, the hand rotating sleeve is movably installed on a fixing jacket, and the hand rotating sleeve is in threaded connection with the push plate, a groove configured to clamp the push plate is formed in the fixing jacket, an elastic medium is arranged between the push plate and the fixing jacket in the groove, an injection pump is connected with the push plate, and the push plate is of an integral structure or a split structure.

* * * * *